(12) United States Patent
Buckley et al.

(10) Patent No.: US 11,530,184 B2
(45) Date of Patent: Dec. 20, 2022

(54) CRYSTAL FORMS OF 2-[4-[(2,3,4-TRIMETHOXYPHENYL) METHYL]PIPERAZIN-1-YL]ETHYL PYRIDINE-3-CARBOXYLATE

(71) Applicant: IMBRIA PHARMACEUTICALS, INC., Boston, MA (US)

(72) Inventors: Neil Buckley, Boston, MA (US); Dan Belmont, Boston, MA (US); Sarah Bethune, Boston, MA (US); Krista Diaz, Boston, MA (US)

(73) Assignee: IMBRIA PHARMACEUTICALS, INC., Boston, MA (US)

( * ) Notice: Subject to any disclaimer, the term of this patent is extended or adjusted under 35 U.S.C. 154(b) by 0 days.

(21) Appl. No.: 17/359,736

(22) Filed: Jun. 28, 2021

(65) Prior Publication Data

US 2021/0403428 A1 Dec. 30, 2021

Related U.S. Application Data

(60) Provisional application No. 63/046,120, filed on Jun. 30, 2020.

(51) Int. Cl.
    *C07D 213/80* (2006.01)

(52) U.S. Cl.
    CPC ........ *C07D 213/80* (2013.01); *C07B 2200/13* (2013.01)

(58) Field of Classification Search
    CPC .................... C07D 213/80; C07B 2200/13
    See application file for complete search history.

(56) References Cited

U.S. PATENT DOCUMENTS

| | | | |
|---|---|---|---|
| 4,100,285 A | 7/1978 | Murai et al. |
| 4,166,452 A | 9/1979 | Generales, Jr. |
| 4,256,108 A | 3/1981 | Theeuwes |
| 4,265,874 A | 5/1981 | Bonsen et al. |
| 4,574,156 A | 3/1986 | Morita et al. |
| 4,845,099 A | 7/1989 | Ruger et al. |
| 4,876,257 A | 10/1989 | Hajos et al. |
| 4,885,300 A | 12/1989 | Press et al. |
| 5,077,288 A | 12/1991 | Lavielle et al. |
| 5,286,728 A | 2/1994 | Ferrini |
| 5,340,809 A | 8/1994 | Gaudry et al. |
| 5,380,726 A | 1/1995 | Ferrini |
| 5,384,319 A | 1/1995 | Ferrini |
| 5,397,780 A | 3/1995 | Mizuno et al. |
| 5,399,557 A | 3/1995 | Mizuno et al. |
| 5,401,743 A | 3/1995 | Rendenbach-Mueller et al. |
| 5,428,038 A | 6/1995 | Chatterjee et al. |
| 5,527,800 A | 6/1996 | Goto et al. |
| 5,591,849 A | 1/1997 | Kato et al. |
| 5,641,779 A | 6/1997 | Halazy et al. |
| 5,770,735 A | 6/1998 | Emonds-Alt et al. |
| 5,776,937 A | 7/1998 | Gante et al. |
| 5,849,745 A | 12/1998 | Wierzbicki et al. |
| 5,856,326 A | 1/1999 | Anthony et al. |
| 5,962,448 A | 10/1999 | Mizuno et al. |
| 5,977,111 A | 11/1999 | Mizuno et al. |
| 6,087,346 A | 7/2000 | Glennon et al. |
| 6,121,267 A | 9/2000 | Glase et al. |
| 6,200,989 B1 | 3/2001 | De Cillis et al. |
| 6,214,841 B1 | 4/2001 | Jackson et al. |
| 6,271,223 B1 | 8/2001 | Mizuno et al. |
| 6,331,623 B1 | 12/2001 | Mizuno et al. |
| 6,528,529 B1 | 3/2003 | Brann et al. |
| 6,562,978 B1 | 5/2003 | Imamura et al. |
| 6,693,099 B2 | 2/2004 | Degenhardt et al. |
| 7,638,531 B2 | 12/2009 | Mutahi et al. |
| 7,666,866 B2 | 2/2010 | Franciskovich et al. |
| 7,772,251 B2 | 8/2010 | Sturzebecher et al. |
| 7,968,538 B2 | 6/2011 | Becker et al. |
| 8,016,783 B2 | 9/2011 | Pastore et al. |
| 8,202,901 B2 | 6/2012 | Lopaschuk et al. |

(Continued)

FOREIGN PATENT DOCUMENTS

| CA | 2170615 A1 | 3/1995 |
|---|---|---|
| CA | 2186010 A1 | 9/1995 |

(Continued)

OTHER PUBLICATIONS

Bhosle, 2006, Mutual Prodrug Concept: Fundamentals and Applications, Indian Journal of Pharmaceutical Sciences, May-Jun., pp. 286-294.

(Continued)

*Primary Examiner* — Timothy R Rozof
(74) *Attorney, Agent, or Firm* — Brown Rudnick LLP; Adam M. Schoen

(57) ABSTRACT

The invention provides polymorphs of a compound of Formula (X):

(X)

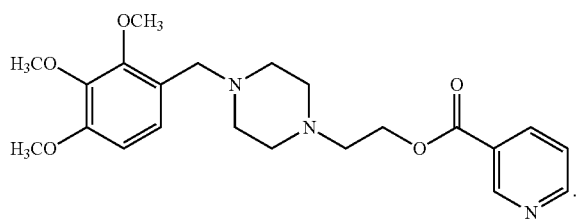

The invention also provided pharmaceutical compositions containing polymorphs of the compound and methods treating conditions in a subject by providing polymorphs of the compound.

22 Claims, 24 Drawing Sheets

(56) References Cited

U.S. PATENT DOCUMENTS

| | | | |
|---|---|---|---|
| 8,461,117 B2 | 6/2013 | Sufi et al. | |
| 8,569,495 B2 | 10/2013 | Chassaing et al. | |
| 8,697,661 B2 | 4/2014 | Kritikou | |
| 9,096,538 B2 | 8/2015 | Nakamura et al. | |
| 9,120,801 B2 | 9/2015 | Alisi et al. | |
| 10,167,258 B2 | 1/2019 | Chuang et al. | |
| 10,556,013 B2 * | 2/2020 | Levin | C07D 213/80 |
| 10,918,728 B2 | 2/2021 | Levin | |
| 2003/0191182 A1 | 10/2003 | Lopaschuk et al. | |
| 2003/0232877 A1 | 12/2003 | Sikorski et al. | |
| 2004/0082564 A1 | 4/2004 | Arrhenius et al. | |
| 2005/0004121 A1 | 1/2005 | Palani et al. | |
| 2007/0004750 A1 | 1/2007 | Lorsbach et al. | |
| 2008/0108618 A1 | 5/2008 | Brann et al. | |
| 2008/0161400 A1 | 7/2008 | Virsik et al. | |
| 2009/0197891 A1 | 8/2009 | Lecanu et al. | |
| 2009/0258064 A1 | 10/2009 | Newell et al. | |
| 2010/0022530 A1 | 1/2010 | Schiemann et al. | |
| 2011/0046370 A1 | 2/2011 | Sim et al. | |
| 2011/0137362 A1 | 6/2011 | Foreman et al. | |
| 2011/0212072 A1 | 9/2011 | Henkel et al. | |
| 2012/0214818 A1 | 8/2012 | Dudley | |
| 2016/0060530 A1 | 3/2016 | Archetti et al. | |
| 2016/0346397 A1 | 12/2016 | Milne et al. | |
| 2017/0008950 A1 | 1/2017 | Capon | |
| 2017/0105414 A1 | 4/2017 | Nakano et al. | |
| 2018/0360975 A1 * | 12/2018 | Levin | A61K 47/55 |
| 2019/0084917 A1 | 3/2019 | Savourey et al. | |
| 2019/0216936 A1 | 7/2019 | Levin | |
| 2020/0138963 A1 | 5/2020 | Levin | |
| 2021/0353617 A1 | 11/2021 | Levin et al. | |

FOREIGN PATENT DOCUMENTS

| | | |
|---|---|---|
| CN | 101747292 B | 7/2011 |
| DE | 2714996 A1 | 10/1977 |
| EP | 0144991 A2 | 6/1985 |
| EP | 0251141 A1 | 1/1988 |
| EP | 615855 A1 | 9/1994 |
| EP | 661266 A1 | 7/1995 |
| EP | 749967 A1 | 12/1996 |
| EP | 1634598 A1 | 3/2006 |
| EP | 1886994 A1 | 2/2008 |
| EP | 2727916 A1 | 5/2014 |
| JP | S57131777 | 8/1982 |
| JP | 2000147773 A | 5/2000 |
| JP | 2006113343 A | 4/2006 |
| JP | 2015017236 A | 1/2015 |
| WO | 1995000165 A1 | 1/1995 |
| WO | 9626196 A2 | 8/1996 |
| WO | 9630054 A1 | 10/1996 |
| WO | 9630343 A1 | 10/1996 |
| WO | 9728141 A1 | 8/1997 |
| WO | 9746549 A1 | 12/1997 |
| WO | 98/58638 A1 | 12/1998 |
| WO | 9950247 A1 | 10/1999 |
| WO | 2001005763 A2 | 1/2001 |
| WO | 2002058698 A2 | 8/2002 |
| WO | 2002064576 A1 | 8/2002 |
| WO | 2003006628 A2 | 1/2003 |
| WO | 2006027223 A1 | 3/2006 |
| WO | 2006117686 A2 | 11/2006 |
| WO | 2006133784 A1 | 12/2006 |
| WO | 2007075629 A2 | 7/2007 |
| WO | 2007096251 A1 | 8/2007 |
| WO | 2007/116074 A1 | 10/2007 |
| WO | 2007/116243 A2 | 10/2007 |
| WO | 2008109991 A1 | 9/2008 |
| WO | 2009015485 A1 | 2/2009 |
| WO | 2009/058818 A2 | 5/2009 |
| WO | 2009066315 A2 | 5/2009 |
| WO | 2009156479 A1 | 12/2009 |
| WO | 2011032099 A1 | 3/2011 |
| WO | 2012049101 A1 | 4/2012 |
| WO | 2015018660 A1 | 2/2015 |
| WO | 2016005576 A1 | 1/2016 |
| WO | 2016107603 A1 | 7/2016 |
| WO | 2018/236745 A1 | 12/2018 |
| WO | 2020/081361 A1 | 4/2020 |

OTHER PUBLICATIONS

Cheng, 2006, Discovery of Potent and Orally Available Malonyl-CoA Decarboxylase Inhibitors as Cardioprotective Agents, J. Med. Chem. 49:4055-4058.

Cheng, 2006, Synthesis and structure-activity relationship of small-molecule malonyl coenzyme A decarboxylase Inhibitors, J. Med. Chem. 49:1517-1525.

Das, 1995, Essential Fatty Acid Metabolism in Patients with Essential Hypertension, Diabetes Mellitus and Coronary Heart Disease, Prostaglandins Leukotrienes and Essential Fatty Acids, 52, 387-391.

Extended European Search Report issued in European Application No. 18821590.9, dated Oct. 5, 2020, 33 pages.

Fillmore, 2014, Malonyl CoA: A Promising Target for the Treatment of Cardiac Disease, Int. Union of Biochem. and Mol. Biol., 66(3):139-146.

Fillmore, 2014, Mitochondrial fatty acid oxidation alterations in heart failure, ischemic heart disease and diabetic cardiomyopathy, Brit. J. Pharmacol. 171:2080-2090.

Folmes, 2005, Fatty Acid Oxidation Inhibitors in the Management of Chronic Complications of Atherosclerosis, Current Atherosclerosis Reports 2005, 7, 63-70.

Gao, 2011, Echocardiography in Mice. Curr Protoc Mouse Biol, 1:71-83.

Gibbs, 1995, Cardiac efficiency, Cardiovasc. Res. 30:627-634.

International Search Report and Written Opinion issued in International Application No. PCT/US2020/034611, dated Oct. 14, 2020, 45 pages.

International Search Report and Written Opinion issued in International Application No. PCT/US2020/34608, dated Oct. 14, 2020, 28 pages.

International Search Report and Written Opinion issued in International Application No. PCT/US2020/34609, dated Oct. 14, 2020, 22 pages.

International Search Report and Written Opinion issued in International Application No. PCT/US2021/039303, dated Nov. 26, 2021, 19 pages.

International Search Report and Written Opinion dated Nov. 5, 2018, for International Patent Application PCT/US2018/038067 with International filing date Jun. 18, 2018 (11 pages).

International Search Report issued in an International Application No. PCT/US2021/030450, dated Sep. 27, 2021, 9 pages.

Kantor, 2000, The Antianginal Drug Trimetazidine Shifts Cardiac Energy Metabolism From Fatty Acid Oxidation to Glucose Oxidation by Inhibiting Mitochondrial Long-Chain 3-Ketoacyl Coenzyme A Thiolase, Circulation Research, 86:580-588.

Kotreka, 2011, Gastroretentive Floating Drug-Delivery Systems: A Critical Review, Critical Reviews in Therapeutic Drug Carrier Systems, 28(1):47-99.

Leriche, 2012, Cleavable linkers in chemical biology, Bioorg. Med. Chem. 20:571-582.

Levy, 2014, Vasodilators in Acute Heart Failure: Review of the Latest Studies, Curr Emerg Hosp Med Rep, 2(2):126-134.

Lopaschuk, 2010, Myocardial Fatty Acid Metabolism in Health and Disease, Phys. Rev. 90:207-258.

Morin, 1998, Evidence for the existence of [3H]-trimetazidine binding sites involved in the regulation of the mitochondrial permeability transition pore, Brit. J. Pharmacol. 123:1385-1394.

Non-Final Office Action issued in U.S. Appl. No. 16/722,691, dated Aug. 19, 2020, 12 pages.

PUBCHEM, CID 2223657, Jul. 15, 2005, pp. 1-14.

PUBCHEM, CID-57503849, Create Date: Aug. 8, 2012, 16 pages.

Reddy, 2006, Lipid Metabolism and Liver Inflammation. II. Fatty liver disease and fatty acid oxidation, Am J Physiol Gastrointest Liver Physiol, 290: G852-G858.

Sabbah, 2005, Metabolic Therapy for Heart Disease: Impact of Trimetazidine, Heart Failure Reviews, 10, 281-288.

(56) References Cited

OTHER PUBLICATIONS

Sannino, 2009, Biodegradable Cellulose-based Hydrogels: Design and Applications, Materials, 2:353-373.
Schipke, 1994, Cardiac efficiency, Basic Res. Cardiol. 89:207-40.
Spiekerkoetter, 2010, Mitochondrial fatty acid oxidation disorders: clinical presentation of long-chain fatty acid oxidation defects before and after newborn screening, J Inherit Metab Dis, 33:527-532.
The Merck Manual List of Diseases https://merckmanuals.com/professional (accessed Jan. 17, 2020), 4 pages.
Trammell, 2016, Nicotinamide riboside is uniquely and orally bioavailable in mice and humans, Nat. Commun. 7:12948, 14 pages.
Visser, 2008, Measuring cardiac efficiency: is it clinically useful? Heart Metab. 39:3-4.
Yuasa, 1988, Pharmacological Studies on the Actions of Trimetazidine and Its Derivatives, The Journal of Kansai Medical University, vol. 40, Issue 1, pp. 89-116.
Extended European Search Report issued in European Application No. 19872680.4, dated Jun. 20, 2022, 7 pages.
Extended European Search Report issued in European Application No. 22169109.0, dated Aug. 30, 2022, 7 pages.

\* cited by examiner

CRYSTAL FORMS OF 2-[4-[(2,3,4-TRIMETHOXYPHENYL) METHYL]PIPERAZIN-1-YL]ETHYL PYRIDINE-3-CARBOXYLATE

CROSS-REFERENCE TO RELATED APPLICATIONS

This application claims the benefit of, and priority to, U.S. Provisional Patent Application No. 63/046,120, filed Jun. 30, 2020, the contents of which are incorporated by reference.

FIELD OF THE INVENTION

The invention relates to crystallographic forms of 2-[4-[(2,3,4-trimethoxyphenyl)methyl]piperazin-1-yl]ethyl pyridine-3-carboxylate.

BACKGROUND

Heart disease is the leading cause of death worldwide, accounting for 15 million deaths across the globe in 2015. In many forms of heart disease, decreased cardiac efficiency stems from changes in mitochondrial energy metabolism. Mitochondria are sub-cellular compartments in which metabolites derived from glucose and fatty acids are oxidized to produce high-energy molecules. Increasing fatty acid oxidation in the heart decreases glucose oxidation, and vice versa. Glucose oxidation is a more efficient source of energy, but in certain types of heart disease, such as heart failure, ischemic heart disease, and diabetic cardiomyopathies, fatty acid oxidation predominates in cardiac mitochondria. As a result, the pumping capacity of the heart is reduced.

CV-8972, which has the IUPAC name 2-[4-[(2,3,4-trimethoxyphenyl)methyl]piperazin-1-yl]ethyl pyridine-3-carboxylate and the following structure:

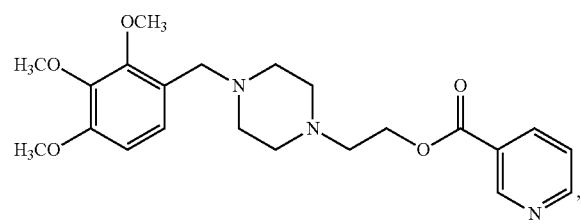 [SMILES: COc1ccc(CN2CCN(CCOC(=O)c3cccnc3)CC2)c(OC)c1OC]

was recently identified as a promising therapeutic candidate for treating or preventing cardiac conditions due to its pharmacokinetic profile.

SUMMARY

Provided herein are crystallographic forms of CV-8972 and compositions containing them. The invention recognizes that crystals of CV-8972 exist in multiple polymorphic forms and that one polymorph, Form A, is the most stable under conditions of ambient temperature and relative humidity. Therefore, Form A crystals of CV-8972 are useful for the manufacture of pharmaceutical compositions. For example, pharmaceutical compositions that contain the Form A polymorph do not require special handling during storage or distribution. In addition, such compositions may retain their efficacy better than compositions containing other polymorphs or mixtures of polymorphs. The invention also provides methods of treating cardiac conditions in subject using CV-8972 polymorphs, such as Form A.

In an aspect, the invention provides crystals comprising a polymorph of a compound of Formula (X):

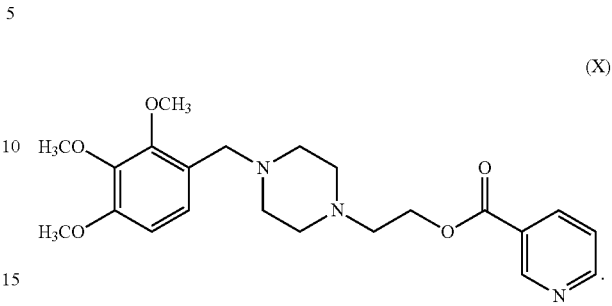

(X)

The polymorph may be Form A, Form B, Form C, Form D, or Form E.

The crystal may be substantially free of one or more other polymorphs. For example, the crystal may include a Form A polymorph and be substantially free of polymorphs of Form B, Form C, Form D, and Form E.

The crystal may include a hydrochloride salt of the compound of Formula (X). The crystal may include the compound of Formula (X) and the hydrochloride ion in a defined stoichiometric ratio. The crystal may include the compound and the hydrochloride ion in a 1:3 stoichiometric ratio.

The crystal may include a hydrated form of the compound of Formula (X). The crystal may include a monohydrate form of the compound. The crystal may include an anhydrous form of the compound.

In another aspect, the invention provides pharmaceutical compositions that include a polymorph of the compound of Formula (X).

The polymorph may be Form A, Form B, Form C, Form D, or Form E.

The composition may be substantially free of one or more other polymorphs. For example, the composition may include a Form A polymorph and be substantially free of polymorphs of Form B, Form C, Form D, and Form E.

The composition may include a hydrochloride salt of the compound of Formula (X). The composition may include the compound of Formula (X) and the hydrochloride ion in a defined stoichiometric ratio. The composition may include the compound and the hydrochloride ion in a 1:3 stoichiometric ratio.

The composition may include a hydrated form of the compound of Formula (X). The composition may include a monohydrate form of the compound. The composition may include an anhydrous form of the compound.

The composition may be formulated for any route or mode of administration. The composition may be formulated for buccal, dermal, enteral, intraarterial, intramuscular, intraocular, intravenous, nasal, oral, parenteral, pulmonary, rectal, subcutaneous, topical, or transdermal administration. The composition may be formulated for administration by injection or with or on an implantable medical device (e.g., stent or drug-eluting stent or balloon equivalents).

The composition may be formulated as a single unit dosage. The composition may be formulated as divided dosages.

The composition may contain a defined dose of the compound. The dose may contain from about 10 mg to about 2000 mg, from about 10 mg to about 1000 mg, from about 10 mg to about 800 mg, from about 10 mg to about 600 mg, from about 10 mg to about 400 mg, from about 10 mg to about 300 mg, from about 10 mg to about 200 mg, from about 25 mg to about 2000 mg, from about 25 mg to about 1000 mg, from about 25 mg to about 800 mg, from about 25 mg to about 600 mg, from about 25 mg to about 400 mg, from about 25 mg to about 300 mg, about 25 mg to about 200 mg, from about 50 mg to about 2000 mg, from about 50 mg to about 1000 mg, from about 50 mg to about 800 mg, from about 50 mg to about 600 mg, from about 50 mg to about 400 mg, from about 50 mg to about 300 mg, about 50 mg to about 200 mg, from about 100 mg to about 2000 mg, from about 100 mg to about 1000 mg, from about 100 mg to about 800 mg, from about 100 mg to about 600 mg, from about 100 mg to about 400 mg, from about 100 mg to about 300 mg, about 100 mg to about 200 mg, from about 200 mg to about 2000 mg, from about 200 mg to about 1000 mg, from about 200 mg to about 800 mg, from about 200 mg to about 600 mg, from about 200 mg to about 400 mg, from about 200 mg to about 300 mg, from about 300 mg to about 2000 mg, from about 300 mg to about 1000 mg, from about 300 mg to about 800 mg, from about 300 mg to about 600 mg, or from about 300 mg to about 400 mg of the compound. The dose may contain about 10 mg, about 25 mg, about 50 mg, about 100 mg, about 200 mg, about 300 mg, or about 400 mg of the compound.

The composition may contain a crystal of the compound of Formula (X). The crystal may have any of the properties described above in relation to crystals of the compound.

In another aspect, the invention provides methods of treating a condition in a subject by providing to a subject having, or at risk of developing, a condition a composition containing a therapeutically effective amount of a polymorph of a compound of Formula (X).

The polymorph may be Form A, Form B, Form C, Form D, or Form E.

The composition may have any of the properties described above in relation to compositions that include the compound of Formula (X), including crystals of the compound.

The composition may be provided by any suitable route or mode of administration. The composition may be provided buccally, dermally, enterally, intraarterially, intramuscularly, intraocularly, intravenously, nasally, orally, parenterally, pulmonarily, rectally, subcutaneously, topically, transdermally, by injection, or with or on an implantable medical device (e.g., stent or drug-eluting stent or balloon equivalents).

The composition may be provided as a single unit dosage. The composition may be provided as divided dosages.

The composition may be provided in one dose per day. The composition may be provided in multiple doses per day. The composition may be provided in two, three, four, five, six, eight, or more doses per day.

The composition may contain a defined dose of the compound, such as any of the doses described above.

The dose or doses may be provided for a defined period. One or more doses may be provided daily for at least one week, at least two weeks, at least three weeks, at least four weeks, at least six weeks, at least eight weeks, at least ten weeks, at least twelve weeks or more.

The condition may be a cardiovascular condition. The cardiovascular condition may be aneurysm, angina, atherosclerosis, cardiomyopathy, cerebral vascular disease, congenital heart disease, coronary artery disease, coronary heart disease, diabetic cardiomyopathy, heart attack, heart disease, heart failure, hypertension, ischemic heart disease, pericardial disease, peripheral arterial disease, rheumatic heart disease, stroke, transient ischemic attacks, or valvular heart disease. The angina may be refractory to other medical interventions.

The condition may be a rheumatic condition. The rheumatic condition may be acute kidney injury, alcoholic cardiomyopathy, angina (e.g., refractory angina and angina associated with heart failure), ankylosing spondylitis, autoimmune-related lung disease, Behcet's Disease, bursitis, cachexia, cardiac fibrosis, chemotherapy chronic fatigue syndrome, claudication (e.g., peripheral claudication), contrast nephropathy, cyanotic heart disease, dermatomyositis, dilated cardiomyopathy, disequilibrium, fibromyalgia, frailty, gout, Gulf War syndrome, heart failure, hypertrophic cardiomyopathy, induced nephropathy, infectious arthritis, inflammatory arthritis, inflammatory eye disease, inflammatory myositis, ischemic cardiomyopathy, juvenile idiopathic arthritis, left ventricular dysfunction, lupus, muscle myopathy, myofascial pain syndrome, myositis, osteoarthritis, osteonecrosis of the jaw, osteoporosis, polymyalgia rheumatica, polymyositis, psoriatic arthritis, pulmonary arterial hypertension, pulmonary fibrosis, a rare muscle disease, rheumatoid arthritis, sarcoidosis, sarcopenia, scleroderma, Sjogren's syndrome, tendinitis, tinnitus, vasculitis, or vertigo.

The condition may fibrosis. The fibrosis may be associated with another disease, disorder, or condition. For example, the fibrosis may include or be associated with adhesive capsulitis, aneurysm, angina, arterial stiffness, arthrofibrosis, atherosclerosis, atrial fibrosis, cardiomyopathy, cerebral vascular disease, cirrhosis, congenital heart disease. coronary artery disease, coronary heart disease, Crohn's disease, cystic fibrosis, diabetic cardiomyopathy, Dupuytren's contracture, endomyocardial fibrosis, glial scar, heart attack, heart failure, high blood pressure (hypertension), idiopathic pulmonary fibrosis, ischemic heart disease, keloid, mediastinal fibrosis, myelofibrosis, nephrogenic systemic fibrosis, old myocardial infarction, pericardial disease, peripheral arterial disease, Peyronie's disease, progressive massive fibrosis, pulmonary fibrosis, radiation-induced lung injury, retroperitoneal fibrosis, rheumatic heart disease, scleroderma, stroke, systemic sclerosis transient ischemic attacks, or valvular heart disease.

The condition may be cancer. The cancer may be bladder cancer, brain cancer, breast cancer, carcinoma, cervical cancer, colon cancer, colorectal cancer, gastric cancer, glioblastoma, glioma, head and neck cancer, kidney cancer, leukemia, liposarcoma, liver cancer, lung cancer, lymphoma, medullablastoma, melanoma, muscle cancer, neuroblastoma, oligoastrocytoma, oligodendroglioma, osteosarcoma, ovarian cancer, pancreatic cancer, paraganglioma, prostate cancer, sarcoma, or thyroid cancer.

In another aspect, the invention provides methods of altering cardiac remodeling by providing to a subject that has developed, or is at risk of developing, cardiac remodeling a composition containing a therapeutically effective amount of a polymorph of a compound of Formula (X).

The polymorph may be Form A, Form B, Form C, Form D, or Form E.

The composition may have any of the properties described above in relation to compositions that include the compound of Formula (X), including crystals of the compound.

The composition may be provided by any suitable route or mode of administration. The composition may be provided buccally, dermally, enterally, intraocular intravenously, nasally, orally, parenterally, pulmonarily, subcutaneously, topically, transdermally, by injection, or with or on an implantable medical device (e.g., stent or drug-eluting stent or balloon equivalents).

The composition may be provided as a single unit dosage. The composition may be provided as divided dosages.

The composition may be provided in one dose per day. The composition may be provided in multiple doses per day. The composition may be provided in two, three, four, five, six, eight, or more doses per day.

The composition may contain a defined dose of the compound, such as any of the doses described above.

The dose or doses may be provided for a defined period. One or more doses may be provided daily for at least one week, at least two weeks, at least three weeks, at least four weeks, at least six weeks, at least eight weeks, at least ten weeks, at least twelve weeks or more.

The cardiac remodeling may be associated with a disease, disorder, or condition. The cardiac remodeling may be associated with a cardiovascular disease. For example, the cardiac remodeling may be associated with aberrant subclavian artery, aortic regurgitation, aortic stenosis, arteriovenous malformation and fistula, atrial septal defect, atrioventricular septal defect, bicuspid aortic valve, cardiomegaly, cardiomyopathy, coarctation of the aorta, complete heart block, concentric hypertrophy, congenital heart defects, congenital heart disease, coronary artery disease, dextrocardia, dextro-transposition of the great arteries, diabetes, diet, double aortic arch, double inlet left ventricle, double outlet right ventricle, Ebstein's anomaly, giant hepatic hemangioma, heart failure, high cholesterol, high-output hemodialysis fistula, hypertension, hypertension, hypoplastic left heart syndrome, hypoplastic right heart syndrome, interrupted aortic arch, levo-transposition of the great arteries, mitral regurgitation, also causing left atrial volume overload, mitral stenosis, myocardial ischemia, obesity, outflow obstruction, partial anomalous pulmonary venous connection, patent ductus arteriosus, pentalogy of Cantrell, persistent truncus arteriosus, pressure overload, pulmonary atresia, pulmonary hypertension, pulmonary regurgitation, pulmonary stenosis, rhabdomyomas, right ventricular volume overload, scimitar syndrome, Shone's syndrome, tetralogy of Fallot, total anomalous pulmonary venous connection, transposition of the great vessels, tricuspid atresia, tricuspid regurgitation, use of tobacco, alcohol, or other drugs, valvular heart disease, ventricular dilation, ventricular hypertrophy, ventricular septal defect, volume overload, and Wolff-Parkinson-White syndrome.

In another aspect, the invention provides uses of crystals containing a polymorph of a compound of Formula (X) for making a medicament.

In embodiments of the use, the polymorph is Form A, Form B, Form C, Form D, or Form E.

In embodiments of the use, the crystal is substantially free of one or more other polymorphs. In embodiments of the use, the crystal includes a Form A polymorph and is substantially free of polymorphs of Form B, Form C, Form D, and Form E.

In embodiments of the use, the crystal includes a hydrochloride salt of the compound of Formula (X). In embodiments of the use, the crystal includes the compound of Formula (X) and the chloride ion in a defined stoichiometric ratio. In embodiments of the use, the crystal includes the compound and the chloride ion in a 1:3 stoichiometric ratio.

In embodiments of the use, the medicament includes a hydrated form of the compound of Formula (X). In embodiments of the use, the medicament includes a monohydrate form of the compound. In embodiments of the use, the medicament includes an anhydrous form of the compound.

In embodiments of the use, the medicament is formulated for buccal, dermal, enteral, intraarterial, intramuscular, intraocular, intravenous, nasal, oral, parenteral, pulmonary, rectal, subcutaneous, topical, or transdermal administration. In embodiments of the use, the medicament is formulated for administration by injection or with or on an implantable medical device (e.g., stent or drug-eluting stent or balloon equivalents).

In embodiments of the use, the medicament is formulated as a single unit dosage. In embodiments of the use, the medicament is formulated as divided dosages.

In embodiments of the use, the medicament contains from about 10 mg to about 2000 mg, from about 10 mg to about 1000 mg, from about 10 mg to about 800 mg, from about 10 mg to about 600 mg, from about 10 mg to about 400 mg, from about 10 mg to about 300 mg, from about 10 mg to about 200 mg, from about 25 mg to about 2000 mg, from about 25 mg to about 1000 mg, from about 25 mg to about 800 mg, from about 25 mg to about 600 mg, from about 25 mg to about 400 mg, from about 25 mg to about 300 mg, about 25 mg to about 200 mg, from about 50 mg to about 2000 mg, from about 50 mg to about 1000 mg, from about 50 mg to about 800 mg, from about 50 mg to about 600 mg, from about 50 mg to about 400 mg, from about 50 mg to about 300 mg, about 50 mg to about 200 mg, from about 100 mg to about 2000 mg, from about 100 mg to about 1000 mg, from about 100 mg to about 800 mg, from about 100 mg to about 600 mg, from about 100 mg to about 400 mg, from about 100 mg to about 300 mg, about 100 mg to about 200 mg, from about 200 mg to about 2000 mg, from about 200 mg to about 1000 mg, from about 200 mg to about 800 mg, from about 200 mg to about 600 mg, from about 200 mg to about 400 mg, from about 200 mg to about 300 mg, from about 300 mg to about 2000 mg, from about 300 mg to about 1000 mg, from about 300 mg to about 800 mg, from about 300 mg to about 600 mg, or from about 300 mg to about 400 mg of the compound. In embodiments of the use, the medicament contains about 10 mg, about 25 mg, about 50 mg, about 100 mg, about 200 mg, about 300 mg, or about 400 mg of the compound.

DETAILED DESCRIPTION

The recently-identified compound CV-8972 holds promise as a therapeutic agent for treating a variety of conditions, including cardiovascular conditions, rheumatic diseases, fibrosis, and cancer. CV-8972, which has the IUPAC name 2-[4-[(2,3,4-trimethoxyphenyl)methyl]piperazin-1-yl]ethyl pyridine-3-carboxylate and the following structure:

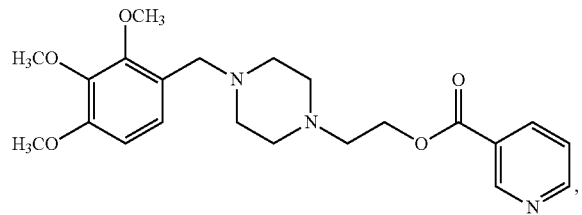 [SMILES: COc1ccc(CN2CCN(CCOC(=O)c3cccnc3)CC2)c(OC)c1OC]

is metabolized in the body into two sets of products that increase mitochondrial energy production in different ways. In an initial reaction, the molecule is split into CV-8814, which has the following structure:

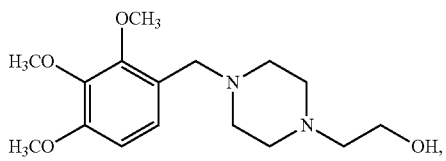 [SMILES: COc1ccc(CN2CCN(CCO)CC2)c(OC)c1OC]

and nicotinic acid. Over time, CV-8814 converted in the body to trimetazidine. Both CV-8814 and trimetazidine inhibit beta-oxidation of fatty acids and therefore shift mitochondrial metabolism toward oxidation of glucose, a more oxygen-efficient source of energy. Nicotinic acid serves as precursor for synthesis of nicotinamide adenine dinucleotide ($NAD^+$). $NAD^+$ promotes mitochondrial respiration to drive ATP synthesis, regardless of whether glucose or fatty acids are used as the carbon source. Thus, the two sets of products that result from breakdown of CV-8972 in vivo act synergistically to stimulate energy production in mitochondria in cardiac tissue and other cell types. CV-8972 and its mechanism of action are described in U.S. Pat. No. 10,556,013, the contents of which are incorporated herein by reference.

The present invention recognizes that crystals of CV-8972 exist in multiple polymorphic forms. One polymorph, Form A, is most stable under conditions of ambient temperature and relative humidity and therefore has particular utility for the manufacture of pharmaceutical compositions. Due to the stability of Form A, compositions containing this polymorph can readily be stored and distributed without loss of therapeutic efficacy. Thus, the invention provides compositions containing polymorphs of crystalline CV-8972, methods of making such compositions, and methods of using them to treat various conditions in a subject.

Polymorphs of CV-8972

As described in the examples below, crystals of CV-8972 may exist in at least five polymorphic forms: Form A, Form B, Form C, Form D, and Form E. Form A is monohydrate, and Forms B, D, and E are anhydrous. Form C was not obtained in purified form, so its hydration state could not be determined.

Crystals may be formed as salts of CV-8972. For example, crystals may be formed as hydrochloride salts of CV-8972.

Figure 1:
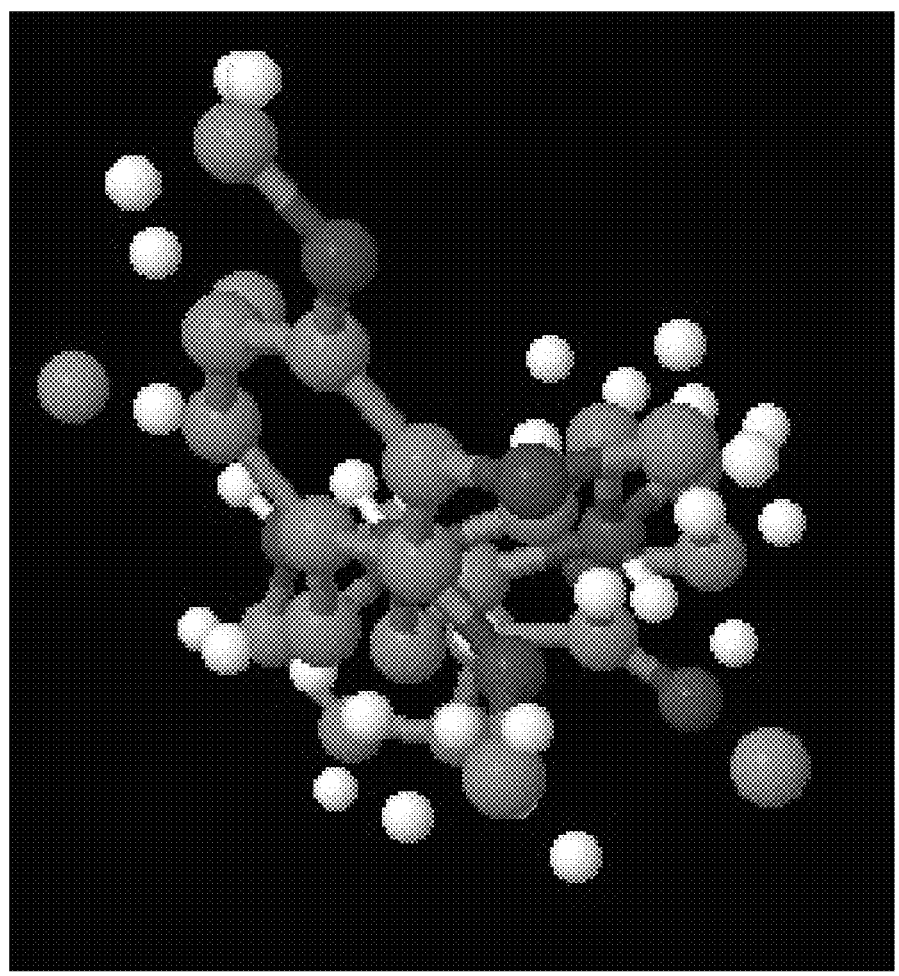
FIG. 1 is a space-filling three-dimensional model of the crystal structure of the Form D polymorph of CV-8972.

FIG. 1 is a space-filling three-dimensional model of the crystal structure of the Form D polymorph of CV-8972. The polymorph is a trihydrochloride salt, and chloride ions are shown in green.

Figure 2:
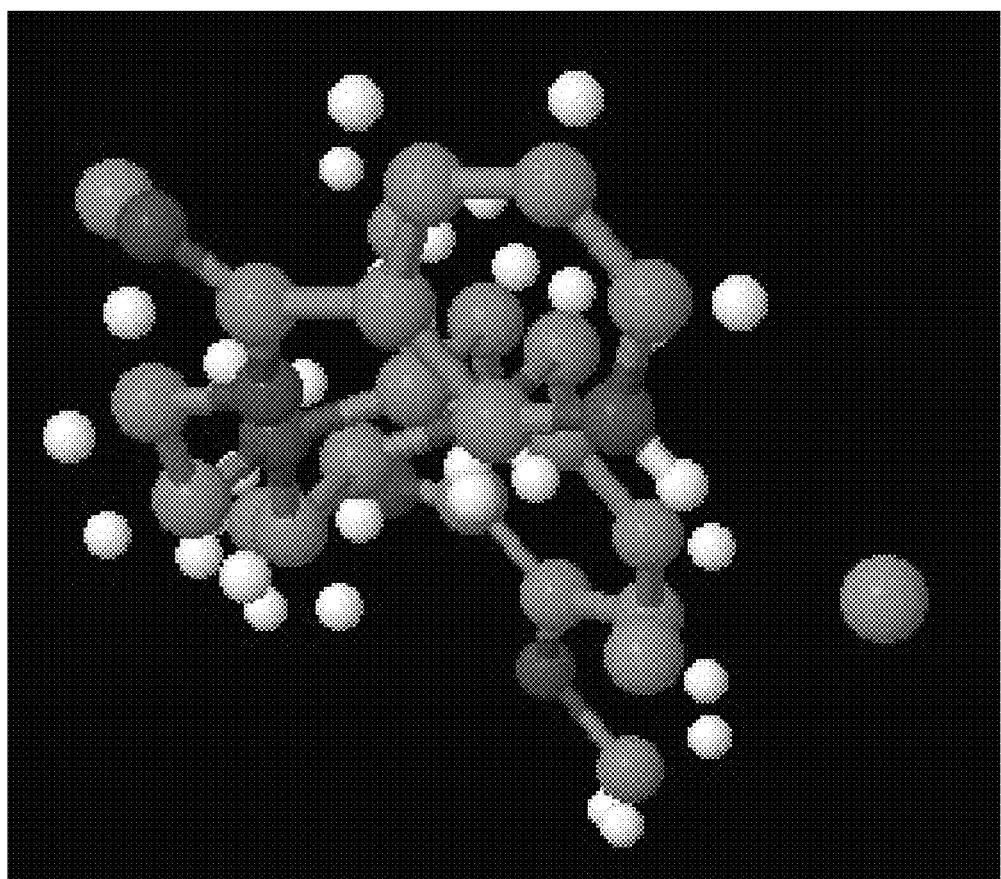
FIG. 2 is a space-filling three-dimensional model of the crystal structure of the Form D polymorph of CV-8972 at room temperature.

FIG. 2 is a space-filling three-dimensional model of the crystal structure of the Form D polymorph of CV-8972 at room temperature. The polymorph is a trihydrochloride salt, and chloride ions are shown in green.

Figure 3:
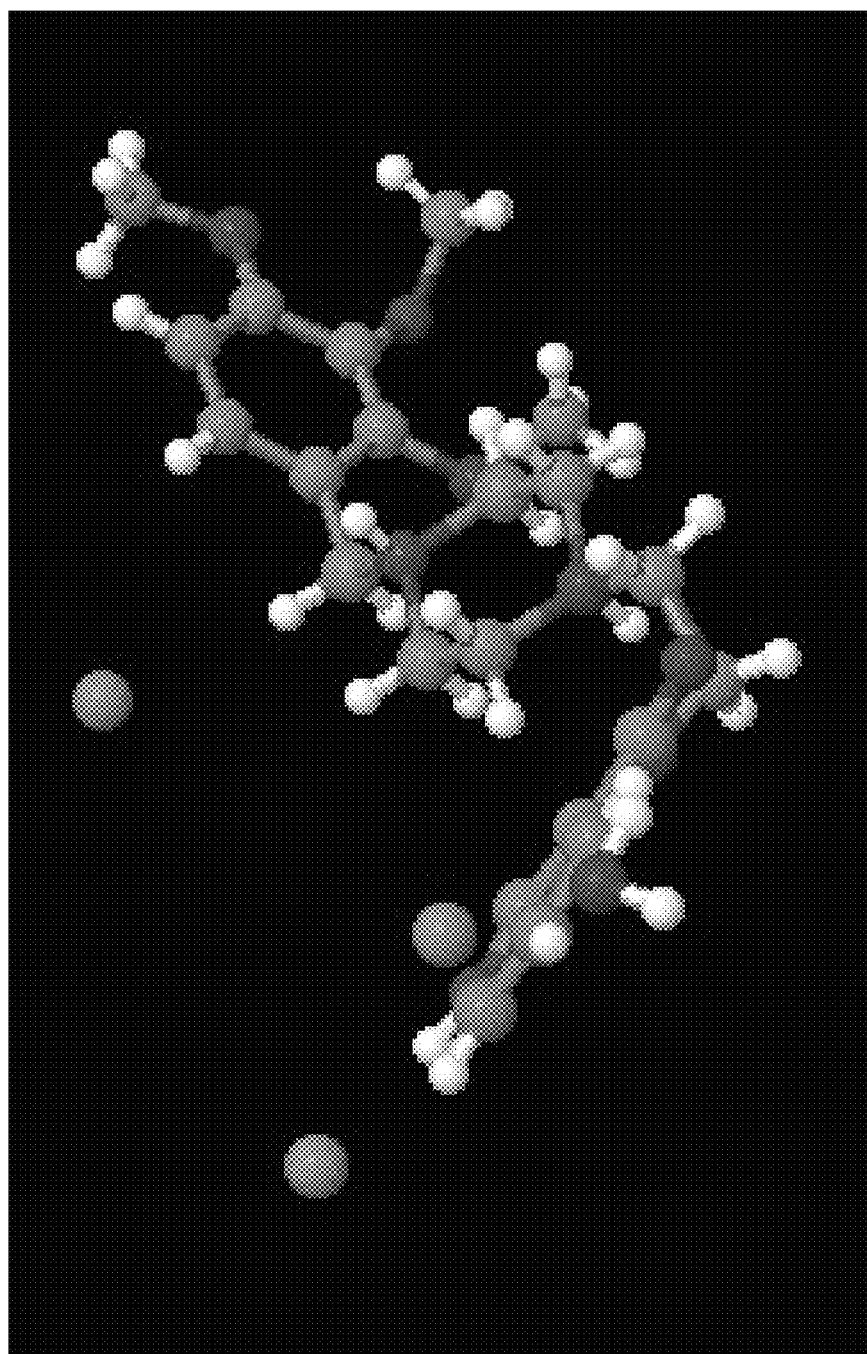
FIG. 3 is a space-filling three-dimensional model of the crystal structure of the Form A polymorph of CV-8972.

FIG. 3 is a space-filling three-dimensional model of the crystal structure of the Form A polymorph of CV-8972. The polymorph is a trihydrochloride salt, and chloride ions are shown in green.

Pharmaceutical Compositions

The invention provides pharmaceutical compositions that contain crystals of a polymorph of CV-8972. For example, the composition may contain CV-8972 crystals in Form A, Form B, Form C, Form D, or Form E. The composition may be substantially free of one or more other polymorphs. For example, the composition may include a Form A polymorph and be substantially free of polymorphs of Form B, Form C, Form D, and Form E.

A composition containing a polymorph of CV-8972 may be substantially free of one or more other polymorphic forms of CV-8972 if the composition contains the predominant polymorph at a defined level of purity. Purity may be expressed as the amount of predominant polymorph as a percentage of the total weight of two of more polymorphs of CV-8972.

In certain embodiments, the total weight is the weight of all polymorphs of CV-8972 in the composition. For example, a composition that contains the Form A polymorph and is substantially free of other polymorphs may contain Form A at a defined weight percentage of all polymorphs of CV-8972 in the composition. For example, the composition may contain Form A at at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of all polymorphs of CV-8972 in the composition.

In certain embodiments, the total weight is the weight of selected polymorphs of CV-8972 in the composition. For example, a composition that contains the Form A polymorph and is substantially free of the Form B polymorph may contain Form A at a defined weight percentage of Forms A and B. For example, the composition may contain Form A at at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of Forms A and B of CV-8972 in the composition. Similarly, a composition that contains the Form A polymorph and is substantially free of the Form B and C polymorphs may contain Form A at a defined weight percentage of Forms A, B, and C. For example, the composition may contain Form A at at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of Forms A, B, and C of CV-8972 in the composition.

Alternatively or additionally, a composition containing a polymorph of CV-8972 may be substantially free of one or more other polymorphic forms of CV-8972 if the composition contains the secondary polymorphs at levels below a defined level. Presence of a secondary polymorphs may be defined as the amount of one or more secondary polymorphs as a percentage of the total weight of two of more polymorphs of CV-8972.

In certain embodiments, the total weight is the weight of all polymorphs of CV-8972 in the composition. For example, a composition that contains the Form A polymorph and is substantially free of other polymorphs may contain all polymorphs other than Form A at a defined weight percentage of all polymorphs of CV-8972 in the composition. For example, the composition may contain all polymorphs other than Form A at below 5% by weight, below 4% by weight, below 3% by weight, below 2% by weight, below 1% by weight, below 0.5% by weight, below 0.4% by weight, below 0.3% by weight, below 0.2% by weight, or below 0.1% by weight of all polymorphs of CV-8972 in the composition.

In certain embodiments, the total weight is the weight of selected polymorphs of CV-8972 in the composition. For example, a composition that contains the Form A polymorph and is substantially free of the Form B polymorph may contain Form B at a defined weight percentage of Forms A and B. For example, the composition may contain Form B at below 5% by weight, below 4% by weight, below 3% by weight, below 2% by weight, below 1% by weight, below 0.5% by weight, below 0.4% by weight, below 0.3% by weight, below 0.2% by weight, or below 0.1% by weight of Forms A and B of CV-8972 in the composition. Similarly, a composition that contains the Form A polymorph and is substantially free of the Form B and Form C polymorphs may contain Forms B and C at a defined weight percentage of Forms A, B, and C. For example, the composition may contain Forms B and C at below 5% by weight, below 4% by weight, below 3% by weight, below 2% by weight, below 1% by weight, below 0.5% by weight, below 0.4% by weight, below 0.3% by weight, below 0.2% by weight, or below 0.1% by weight of Forms A, B, and C of CV-8972 in the composition.

The composition may include a hydrochloride salt of a CV-8972 polymorph. The composition may include CV-8972 and the chloride ion a defined stoichiometric ratio. The composition may include CV-8972 and the chloride ion in a 1:3 stoichiometric ratio.

The composition may include a hydrated form of CV-8972. The composition may include a monohydrate form of CV-8972, such as the Form A polymorph. The composition may include an anhydrous form of CV-8972, such as a Form B, Form D, or Form E polymorph.

The composition may be formulated for any route or mode of administration. The composition may be formulated for buccal, dermal, enteral, intraarterial, intramuscular, intraocular, intravenous, nasal, oral, parenteral, pulmonary, rectal, subcutaneous, topical, or transdermal administration. The composition may be formulated for administration by injection or with or on an implantable medical device (e.g., stent or drug-eluting stent or balloon equivalents).

The composition may be formulated as a single unit dosage. The composition may be formulated as divided dosages.

The composition may contain a defined dose of CV-8972. The dose may contain from about 10 mg to about 2000 mg, from about 10 mg to about 1000 mg, from about 10 mg to about 800 mg, from about 10 mg to about 600 mg, from about 10 mg to about 400 mg, from about 10 mg to about 300 mg, from about 10 mg to about 200 mg, from about 25 mg to about 2000 mg, from about 25 mg to about 1000 mg, from about 25 mg to about 800 mg, from about 25 mg to about 600 mg, from about 25 mg to about 400 mg, from about 25 mg to about 300 mg, about 25 mg to about 200 mg, from about 50 mg to about 2000 mg, from about 50 mg to about 1000 mg, from about 50 mg to about 800 mg, from about 50 mg to about 600 mg, from about 50 mg to about 400 mg, from about 50 mg to about 300 mg, about 50 mg to about 200 mg, from about 100 mg to about 2000 mg, from about 100 mg to about 1000 mg, from about 100 mg to about 800 mg, from about 100 mg to about 600 mg, from about 100 mg to about 400 mg, from about 100 mg to about 300 mg, about 100 mg to about 200 mg, from about 200 mg to about 2000 mg, from about 200 mg to about 1000 mg, from about 200 mg to about 800 mg, from about 200 mg to about 600 mg, from about 200 mg to about 400 mg, from about 200 mg to about 300 mg, from about 300 mg to about 2000 mg, from about 300 mg to about 1000 mg, from about 300 mg to about 800 mg, from about 300 mg to about 600 mg, or from about 300 mg to about 400 mg of CV-8972. The dose may contain about 10 mg, about 25 mg, about 50 mg, about 100 mg, about 200 mg, about 300 mg, or about 400 mg of CV-8972.

A pharmaceutical composition containing a polymorph of CV-8972 may be in a form suitable for oral use, such as tablets, troches, lozenges, fast-melts, dispersible powders or granules, or capsules. Compositions intended for oral use may be prepared according to any method known in the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the polymorph in admixture with non-toxic pharmaceutically acceptable excipients. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid, or talc. Preparation and administration of pharmaceutical compositions is discussed in U.S. Pat. No. 6,214,841 and U.S. Patent Publication No. 2003/0232877, the contents of each of which are incorporated by reference herein. Formulations for oral use may also be presented as hard gelatin capsules in which the compounds are mixed with an inert solid diluent, such as calcium carbonate, calcium phosphate or kaolin. The formulation may allow controlled release of the polymorph of CV-8972 in the gastrointestinal tract by encapsulating the polymorph in an enteric coating.

Dispersible powders and granules provide the compounds in admixture with a dispersing or wetting agent, suspending agent and one or more preservatives. Suitable dispersing or wetting agents and suspending agents are exemplified, for example sweetening, flavoring and coloring agents, may also be present.

Pharmaceutical compositions may contain mixtures that include erodible polymers that promote swelling of the mixture in an aqueous environment. An erodible polymer is any polymer that breaks down inside the body within a physiologically relevant time frame. The erodible polymer may have other characteristics that promote the gradual release of the polymorphic form of CV-8972 from the mixture. For example and without limitation, the polymer may be one or more of the following: biocompatible, i.e., not harmful to living tissue; hydrophilic; hygroscopic; tending to form a hydrogel.

Without wishing to be bound by theory, the polymer-containing mixtures may promote gradual release by one or more mechanisms. For example, swelling of the mixture by absorption of water may facilitate diffusion of the polymorphic form of CV-8972 from the mixture. Degradation of the polymer may also allow the polymorphic form of CV-8972 to be released from the mixture. Osmotic pressure due the high concentration gradient of compound between the inside and outside of the mixture may also contribute to diffusion of the polymorphic form of CV-8972 from the mixture.

For example and without limitation, the polymer may be a cellulose derivative, a gelatin derivative, e.g., a cross-linked gelatin derivative, or a polyester derivative.

Derivatives of cellulose, is a linear chain β(1→4) linked D-glucose units, include polymers that contain substitutions on one or more of the hydroxyl groups of each glucose unit. Substituents may be organic or inorganic and are typically attached via ester or ether linkages. Cellulose ester derivatives include carboxymethyl cellulose (CMC), e.g., sodium carboxymethyl cellulose, ethyl cellulose, ethyl hydroxyethyl cellulose, ethyl methyl cellulose, hydroxyethyl cellulose, hydroxyethyl methyl cellulose, hydroxypropyl cellulose (HPC), hydroxypropyl methylcellulose (HPMC), and methylcellulose. Cellulose ether derivatives include cellulose acetate, cellulose acetate butyrate, cellulose acetate propionate, cellulose propionate, cellulose sulfate, cellulose triacetate, and nitrocellulose. The use of cellulose-based polymers to form biodegradable hydrogels is known in the art and described in, for example, Sannino, et al., Biodegradable Cellulose-based Hydrogels: Design and Applications, Materials 2009, 2, 353-373; doi:10.3390/ma2020353, the contents of which are incorporated herein by reference.

The mixture may contain multiple polymers or multiple polymeric forms of the same polymer. For example, HPMC polymeric forms may differ in a variety of physical properties, including viscosity, degree of methoxyl substitution, degree of hydroxypropoxyl substitution, or average molecule weight.

The viscosity of a HMPC polymeric form may be determined by testing under standard conditions, including the concentration of HMPC in the solution and the temperature of the solution. For example and without limitation, the HPMC concentration may be 1%, 1.5%, 2%, 2.5%, or 3%. For example and without limitation, the temperature of the solution may be 15° C., 16° C., 17° C., 18° C., 19° C., 20° C., 21° C., 22° C., 23° C., 24° C., or 25° C.

A polymeric form of a cellulose derivative, such as HPMC, may have a defined viscosity. For example and without limitation, a polymeric form of HPMC may have a viscosity of from about 2 cP to about 4 cP, from about 4 cP to about 6 cP, from about 5 cP to about 8 cP, from about 12 cP to about 18 cP, from about 40 cP to about 60 cP, from about 80 cP to about 120 cP, from about 300 cP to about 500 cP, from about 1200 cP to about 2400 cP, from about 2500 cP to about 5000 cP, from about 9000 cP to about 18,000 cP, from about 12,000 cP to about 24,000 cP, from about 12,000 cP to about 24,000 cP, from about 75,000 cP to about 150,000 cP, at least about 2 cP at least about 4 cP at least about 5 cP at least about 12 cP at least about 40 cP at least about 80 cP at least about 300 cP at least about 1200 cP at least about 2500 cP at least about 9000 cP at least about 12,000 cP at least about 12,000 cP at least about 75,000 cP less than about 4 cP, less than about 6 cP, less than about 8 cP, less than about 18 cP, less than about 60 cP, less than about 120 cP, less than about 500 cP, less than about 2400 cP, less than about 5000 cP, less than about 18,000 cP, less than about 24,000 cP, less than about 24,000 cP, or less than about 150,000 cP for a 2% aqueous solution of the polymeric form at 20° C.

Polymeric forms of cellulose derivatives, such as HPMC, may vary in their degree of substitution of the glucose units. The degree of substitution may be expressed as a weight percentage of the substituent or as a molar ratio of substituent to glucose unit. For a cellulose derivative that has two different substituents, such as HPMC, the polymeric form may be described by the degree of substitution for each substituent.

Each polymeric form of HPMC may independently have a defined degree of methoxyl substitution. For example and without limitation, the degree of methoxyl substitution may be from about 19% to about 24%, from about 22% to about 24%, from about 27% to about 30%, from about 27% to about 30%, or from about 28% to about 32%.

Each polymeric form of HPMC may independently have a defined degree of hydroxypropoxyl substitution. For example and without limitation, the degree of hydroxypropoxyl substitution may be from about 4% to about 8%, from about 7% to about 10%, from about 7% to about 12%, from about 8% to about 10%, from about 8% to about 11%, or from about 9% to about 12%.

Each polymeric form of HPMC may independently have a defined average molecular weight. The average molecular weight may be about 10 kDa, about 13 kDa, about 20 kDa, about 26 kDa, about 41 kDa, about 63 kDa, about 86 kDa, about 110 kDa, about 120 kDa, about 140 kDa, about 180 kDa, or about 220 kDa.

When multiple forms of a polymer, such as HPMC, are present, one or more polymeric forms may be present in a defined amount. For example and without limitation, a polymer, such as HPMC, may contain about 50%, about 60%, about 70%, about 80%, about 90%, about 95%, about 96%, about 97%, about 98%, about 99%, at least 50%, at least 60%, at least 70%, at least 80%, at least 90%, at least 95%, at least 96%, at least 97%, at least 98%, or at least 99% by weight of one polymeric form.

Pharmaceutical compositions may include modified-release formulations that contain one or more polymorphic forms of CV-8972. The formulations contain mixtures that include one or more polymorphic forms of CV-8972 and one or more erodible polymers that promote swelling of the mixture in an aqueous environment. The hygroscopic and erodible properties of the polymers may allow the mixture to form a hydrogel that slowly breaks down in the digestive tract of the subject. Consequently, the mixture promotes the steady release of the polymorphic form of CV-8972 and metabolic products thereof into circulation.

The mixture may contain a defined amount of the polymorphic form of CV-8972. The mixture may contain at least 5%, at least 10%, at least 20%, at least 30%, at least 40%, at least 50%, at least 60%, at least 70%, or at least 80% by weight of the polymorphic form of CV-8972.

The mixture may contain the polymorphic form of CV-8972 and the polymer in a defined weight ratio. For example and without limitation, the mixture may contain the polymorphic form of CV-8972 and the polymer in a weight ratio of about 1:5, about 1:4, about 1:3, about 1:2, about 1:1, about 3:2, about 2:1, about 3:1, about 4:1, about 5:1, from about 1:100 to about 100:1, from about 1:100 to about 50:1, from about 1:100 to about 20:1, from about 1:100 to about 10:1, from about 1:100 to about 5:1, from about 1:100 to about 2:1, from about 1:50 to about 100:1, from about 1:50 to about 50:1, from about 1:50 to about 20:1, from about 1:50 to about 10:1, from about 1:50 to about 5:1, from about 1:50 to about 2:1, from about 1:20 to about 100:1, from about 1:20 to about 50:1, from about 1:20 to about 20:1, from about 1:20 to about 10:1, from about 1:20 to about 5:1, from about 1:20 to about 2:1, from about 1:10 to about 100:1, from about 1:10 to about 50:1, from about 1:10 to about 20:1, from about 1:10 to about 10:1, from about 1:10 to about 5:1, from about 1:10 to about 2:1, from about 1:5 to about 100:1, from about 1:5 to about 50:1, from about 1:5 to about 20:1, from about 1:5 to about 10:1, from about 1:5 to about 5:1, from about 1:5 to about 2:1, from about 1:3 to about 100:1, from about 1:3 to about 50:1, from about 1:3 to about 20:1, from about 1:3 to about 10:1, from about 1:3 to about 5:1, or from about 1:3 to about 2:1.

The pharmaceutical composition may be formulated for a particular route of administration. The pharmaceutical may be formulated for oral, enteral, intravenous, or rectal administration.

The pharmaceutical composition may be formulated as a unit dosage containing a defined amount of the polymorphic form of CV-8972. The unit dosage may contain about 5 mg, about 10 mg, about 20 mg, about 50 mg, about 100 mg, about 200 mg, about 500 mg, from about 5 mg to about 10 mg, from about 5 mg to about 20 mg, from about 5 mg to about 50 mg, from about 5 mg to about 100 mg, from about 5 mg to about 200 mg, from about 5 mg to about 500 mg, from about 10 mg to about 20 mg, from about 10 mg to about 50 mg, from about 10 mg to about 100 mg, from about 10 mg to about 200 mg, from about 10 mg to about 500 mg, from about 20 mg to about 50 mg, from about 20 mg to about 100 mg, from about 20 mg to about 200 mg, from about 20 mg to about 500 mg, from about 50 mg to about 100 mg, from about 50 mg to about 200 mg, from about 50 mg to about 500 mg, from about 100 mg to about 200 mg, from about 100 mg to about 500 mg, or from about 200 mg to about 500 mg of the polymorphic form of CV-8972.

The pharmaceutical composition may be formulated such that it produces a defined value for one or more parameters, as described below in relation to methods of the invention. For example and without limitation, the parameter may be $C_{max}$, the interval between administration and achieving $C_{max}$, $T_{1/2}$, or AUC.

Pharmaceutical compositions of the invention may contain excipients. For example and without limitation, the composition may contain sweetening agents, flavoring agents, coloring agents, or preserving agents. The compositions may contain one or more of mannitol, starch, and magnesium stearate.

Providing a Polymorph of CV-8972 to a Subject

The invention provides methods of treating a condition in a subject by providing a polymorph of CV-8972. The polymorph may be Form A, Form B, Form C, Form D, or Form E. The polymorph of CV-8972 may be provided in a pharmaceutical composition, as described above. In certain embodiments of the methods, only a polymorph of Form A is provided.

The polymorph of CV-8972 may be provided by any suitable route or mode of administration. For example and without limitation, the polymorph of CV-8972 may be provided buccally, dermally, enterally, intraarterially, intramuscularly, intraocularly, intravenously, nasally, orally, parenterally, pulmonarily, rectally, subcutaneously, topically, transdermally, by injection, or with or on an implantable medical device (e.g., stent or drug-eluting stent or balloon equivalents).

The polymorph of CV-8972 may be provided according to a dosing regimen. A dosing regimen may include a dosage, a dosing frequency, or both.

Doses may be provided at any suitable interval. For example and without limitation, doses may be provided once per day, twice per day, three times per day, four times per day, five times per day, six times per day, eight times per day, once every 48 hours, once every 36 hours, once every 24 hours, once every 12 hours, once every 8 hours, once every 6 hours, once every 4 hours, once every 3 hours, once every two days, once every three days, once every four days, once every five days, once every week, twice per week, three times per week, four times per week, or five times per week.

The dose may contain a defined amount of CV-8972 that improves cardiac mitochondrial function, such as any of the doses described above in relation to pharmaceutical compositions containing a polymorph of CV-8972.

The dose may be provided in a single dosage, i.e., the dose may be provided as a single tablet, capsule, pill, etc. Alternatively, the dose may be provided in a divided dosage, i.e., the dose may be provided as multiple tablets, capsules, pills, etc.

The dosing may continue for a defined period. For example and without limitation, doses may be provided for at least one week, at least two weeks, at least three weeks, at least four weeks, at least six weeks, at least eight weeks, at least ten weeks, at least twelve weeks or more.

The subject may be a human. The subject may be a human that has a cardiovascular condition, rheumatic condition, fibrosis, or cancer. The subject may be a human that is at risk of developing a cardiovascular condition, rheumatic condition, fibrosis, or cancer. A subject may be at risk of developing a condition if the subject does not meet established criteria for diagnosis of the condition but has one or more symptoms, markers, or other factors that indicate the subject is likely to meet the diagnostic criteria for the condition in the future. The subject may be a pediatric, a newborn, a neonate, an infant, a child, an adolescent, a pre-teen, a teenager, an adult, or an elderly subject. The subject may be in critical care, intensive care, neonatal intensive care, pediatric intensive care, coronary care, cardiothoracic care, surgical intensive care, medical intensive care, long-term intensive care, an operating room, an ambulance, a field hospital, or an out-of-hospital field setting.

Conditions that May be Treated with a Polymorph of CV-8972

The invention provides methods of treating a condition in a subject by providing a polymorph of CV-8972. The condition may be any disease, disorder, or condition for which increasing mitochondrial energy production provides a therapeutic benefit.

The condition may be a cardiac condition. For example and without limitation, the cardiac condition may be aneurysm, angina, atherosclerosis, cardiomyopathy, cerebral vascular disease, congenital heart disease. coronary artery disease (CAD), coronary heart disease, diabetic cardiomyopathy, heart attack, heart disease, heart failure, high blood pressure (hypertension), ischemic heart disease, pericardial disease, peripheral arterial disease, refractory angina, rheumatic heart disease, stable angina, stroke, transient ischemic attack, unstable angina, or valvular heart disease.

Angina pectoris (angina) is chest pain or pressure that is typically due to insufficient blood flow to the heart muscle. The pain or discomfort is retrosternal or left-sided and may radiate to the left arm, neck, jaw, or back. Several classifications of angina are known.

Stable angina, also called effort angina, is related to myocardial ischemia. In stable angina, chest discomfort and associated symptoms are usually triggered by some physical activity, such as running or walking, but symptoms are minimal or non-existent when the patient is at rest or has taken sublingual nitroglycerin. Symptoms typically abate several minutes after activity and recur when activity resumes. Symptoms may also be induced by cold weather, heavy meals, and emotional stress.

Unstable angina is angina that changes or worsens. Unstable angina has at least one of the following features: (1) it occurs at rest or with minimal exertion, usually lasting more than 10 minutes, (2) it is severe and of new onset, i.e., within the prior 4-6 weeks, and (3) it occurs with a crescendo pattern, i.e., distinctly more severe, prolonged, or frequent than before.

Cardiac syndrome X, also called microvascular angina, is angina-like chest pain, in the context of normal epicardial coronary arteries on angiography. Its primary cause is unknown, but factors apparently involved are endothelial dysfunction and reduced flow in the tiny resistance blood vessels of the heart. Microvascular angina may be part of the pathophysiology of ischemic heart disease.

Refractory angina is a chronic condition (>3 months in duration) in which angina (1) occurs in the context of coronary artery disease (CAD), (2) cannot be controlled by a combination of optimal medical therapy, angioplasty, or bypass surgery, and (3) in which reversible myocardial ischemia has been clinically established to be the cause of the symptoms.

Providing a polymorph of CV-8972 may improve cardiac efficiency in the subject. A variety of definitions of cardiac efficiency exist in the medical literature. See, e.g., Schipke, J. D. Cardiac efficiency, Basic Res. Cardiol. 89:207-40 (1994); and Gibbs, C. L. and Barclay, C. J. Cardiac efficiency, Cardiovasc. Res. 30:627-634 (1995), incorporated herein by reference. One definition of cardiac mechanical efficiency is the ratio of external cardiac power to cardiac energy expenditure by the left ventricle. See Lopaschuk G. D., et al., Myocardial Fatty Acid Metabolism in Health and Disease, Phys. Rev. 90:207-258 (2010), incorporated herein by reference. Another definition is the ratio between stroke work and oxygen consumption, which ranges from 20-25% in the normal human heart. Visser, F., Measuring cardiac efficiency: is it useful? Hear Metab. 39:3-4 (2008), incorporated herein by reference. Another definition is the ratio of the stroke volume to mean arterial blood pressure. Any suitable definition of cardiac efficiency may be used to measure the effects of compounds of the invention A polymorph of CV-8972 may be used to treat a rheumatic disease, disorder, or condition. As used herein, a rheumatic disease, disorder, or condition is any condition that affects the joints, tendons, ligaments, bones, muscles, or connective tissue or is associated with pain in or more of such tissues. The rheumatic disease, disorder, or condition may primarily affect the joints, tendons, ligaments, bones, muscles, or connective tissue. Examples of such conditions include ankylosing spondylitis, autoimmune-related lung disease, Behcet's Disease, bursitis, chronic fatigue syndrome, dermatomyositis, fibromyalgia, gout, Gulf War syndrome, infectious arthritis, inflammatory arthritis, inflammatory eye disease, inflammatory myositis, juvenile idiopathic arthritis, lupus, myofascial pain syndrome, osteoarthritis, osteonecrosis of the jaw, osteoporosis, polymyalgia rheumatica, polymyositis, psoriatic arthritis, rheumatoid arthritis, sarcoidosis, scleroderma, Sjogren's syndrome, tendinitis, and vasculitis.

The rheumatic disease, disorder, or condition may primarily affect the cardiovascular system and have secondary effects on the joints, tendons, ligaments, bones, muscles, or connective tissue. For example and without limitation, the condition may be alcoholic cardiomyopathy, aneurysm, angina (including refractory angina and angina in the context of heart failure), atherosclerosis, cardiac fibrosis, cardiomyopathy, cerebral vascular disease, claudication (e.g., peripheral claudication) congenital heart disease. coronary artery disease, coronary heart disease, cyanotic heart disease, diabetic cardiomyopathy, dilated cardiomyopathy, heart attack, heart failure, high blood pressure (hypertension), hypertrophic cardiomyopathy, ischemic cardiomyopathy, ischemic heart disease, left ventricular dysfunction, pericardial disease, peripheral arterial disease, rheumatic heart disease, stroke, transient ischemic attacks, or valvular heart disease.

The rheumatic disease, disorder, or condition may be a rare muscle disease. For example and without limitation, the condition may be CAV3-related distal myopathy, Duchenne Muscular Dystrophy, hypertrophic cardiomyopathy, isolated hyperCKemia, limb-girdle muscular dystrophy 1C, muscle myopathy, myositis, or rippling muscle disease. The rare muscle disease may be associated with a mutation in BICD2, CAV3, or DMD.

The rheumatic disease, disorder, or condition may be a glycogen storage disease. For example and without limitation, the glycogen storage disease may be aldolase A deficiency, Andersen disease, Cori's disease, Fanconi-Bickel syndrome, Hers' disease, Lafora disease, McArdle disease, Pompe's disease, Tarui's disease, or von Gierke's disease. The glycogen storage disease may be associated with a deficiency in an enzyme or protein, such as acid alpha-glucosidase, aldolase A, β-enolase, glucose transporter, glucose-6-phosphatase, glycogen branching enzyme, glycogen debranching enzyme, glycogen synthase, glycogenin-1, liver glycogen phosphorylase, muscle glycogen phosphorylase, muscle lactate dehydrogenase, muscle phosphofructokinase, muscle phosphoglycerate mutase, phosphoglycerate mutase, or phosphorylase kinase. The glycogen storage disease may be associated with a mutation in a gene, such as AGL, ALDOA, ENO3, G6PC, GAA, GBE1, GLUT2, GYG1, GYS2, LDHA, PGAM2, PGAM2, PHKA1, PHKA2, PHKB, PHKG2, PKFM, PYGL, PYGM, or SLC37A4.

The rheumatic disease, disorder, or condition may be another condition that affects the joints, tendons, ligaments, bones, muscles, or connective tissue, such as acute kidney injury, cachexia, chemotherapy induced nephropathy, contrast nephropathy, disequilibrium, frailty, pulmonary arterial hypertension, pulmonary fibrosis, sarcopenia, tinnitus, or vertigo.

A polymorph of CV-8972 may be used to treat fibrosis or a disease, disorder, or condition associated with fibrosis. In particular, the methods are useful for treating diseases, disorders, or conditions in which fibrosis in an organ or tissue is associated with reduced energy production by that organ or tissue. The fibrosis may affect any organ or tissue, such as the heart, lungs, liver, brain, cardiovascular system, joints, gastrointestinal system, limbs, digits, skin, bone marrow, or penis.

The fibrosis may be associated with another condition, e.g., it may be secondary to another condition, or it may lead to the other condition. For example and without limitation, the fibrosis may include or be associated with adhesive capsulitis, aneurysm, angina, arterial stiffness, arthrofibrosis, atherosclerosis, atrial fibrosis, cardiomyopathy, cerebral vascular disease, cirrhosis, congenital heart disease. coronary artery disease, coronary heart disease, Crohn's disease, cystic fibrosis, diabetic cardiomyopathy, Dupuytren's contracture, endomyocardial fibrosis, glial scar, heart attack, heart failure, high blood pressure (hypertension), idiopathic pulmonary fibrosis, ischemic heart disease, keloid, mediastinal fibrosis, myelofibrosis, nephrogenic systemic fibrosis, old myocardial infarction, pericardial disease, peripheral arterial disease, Peyronie's disease, progressive massive fibrosis, pulmonary fibrosis, radiation-induced lung injury, retroperitoneal fibrosis, rheumatic heart disease, scleroderma, stroke, systemic sclerosis transient ischemic attacks, or valvular heart disease.

A polymorph of CV-8972 may be used to treat cancer. For example and without limitation, the cancer may be bladder cancer, brain cancer, breast cancer, carcinoma, cervical cancer, colon cancer, colorectal cancer, gastric cancer, glioblastoma, glioma, head and neck cancer, kidney cancer, leukemia, liposarcoma, liver cancer, lung cancer, lymphoma, medullablastoma, melanoma, muscle cancer, neuroblastoma, oligoastrocytoma, oligodendroglioma, osteosarcoma, ovarian cancer, pancreatic cancer, paraganglioma, prostate cancer, sarcoma, or thyroid cancer.

EXAMPLES

Example 1

Summary

A comprehensive polymorph screening for CV-8972, which has the structure of Formula (X), was undertaken. The CV-8972 starting material was characterized by X-ray powder diffraction (XRPD), thermogravimetric analysis (TGA), differential scanning calorimetry (DSC), dynamic vapor sorption (DVS), and polarized light microscopy (PLM). The data showed that the material is crystalline in nature and has similar XRPD pattern to that of the Form A. Starting with Form A, polymorph/single crystal screening experiments were set up under 34 conditions using methods of vapor diffusion, slow evaporation, and cooling crystallization. Five unique XRPD patterns were observed, which include Form A, Form B, Forms A+C, Form D, and Form E. Form A is monohydrate form as confirmed by single crystal structure. Form D is anhydrous, and it was also confirmed by single crystal structure. Form E is an anhydrous form produced through dehydration of Form A at ~90° C. Form B is a known anhydrate from a separate study. Form C was not obtained in the pure form during the study but rather appeared as a mixture of Forms A+C. Water activity analysis indicated that Form E converts to Form A under all conditions tested. In addition, when Form E was exposed to ambient temperature and humidity, it showed partial conversion to Form A. Further, the results from slurry competition between both anhydrous Forms D and E also indicated that both forms converted to Form A during the experiments. These results suggest that the Form A is the most stable form at the ambient temperature and humidity.

Characterization of Form A

The starting material of CV-8972 was characterized using X-ray powder diffraction (XRPD), thermogravimetric analysis (TGA), differential scanning calorimetry (DSC), and polarized light microscopy (PLM).

Figure 4:
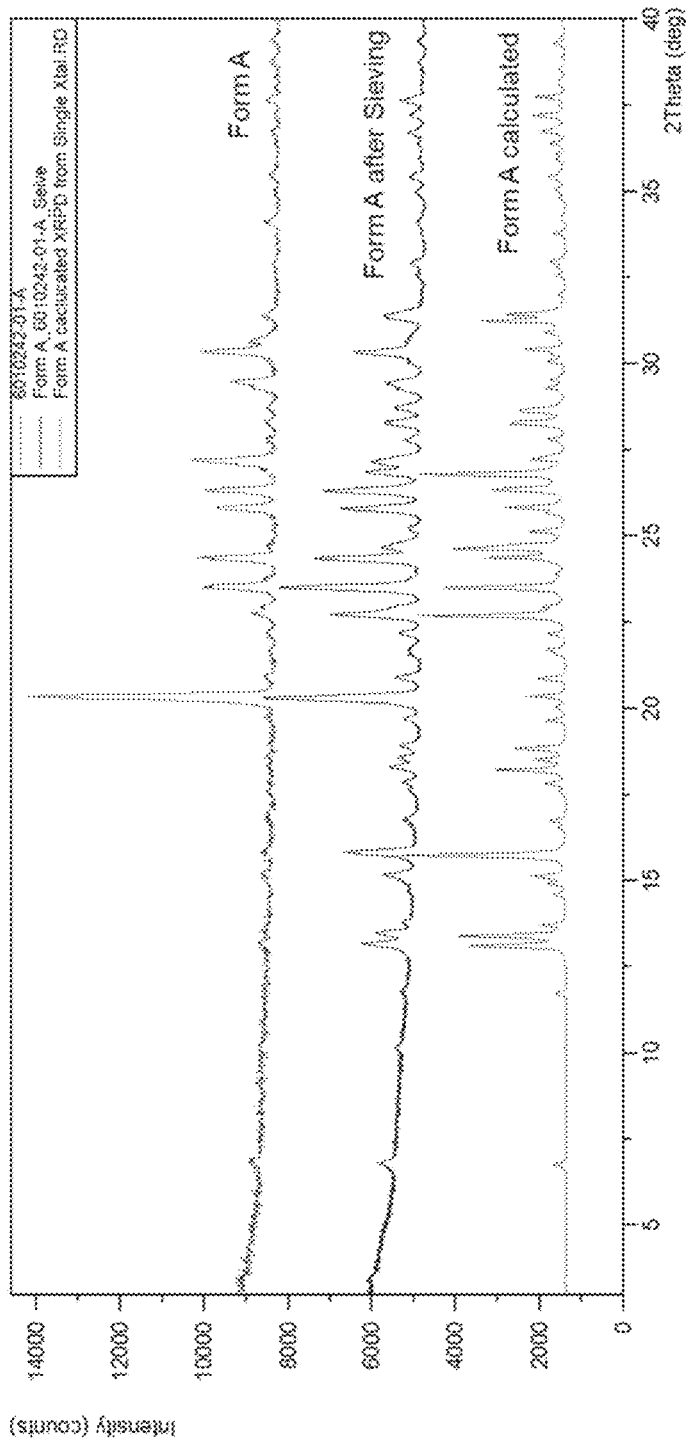
FIG. 4 is an XRPD diffractogram of the CV-8972 starting material.

FIG. 4 is an XRPD diffractogram of the CV-8972 starting material. The XRPD results suggested high crystallinity of the starting material. Comparison of the XRPD of the starting material with previously known polymorphs indicated that it is Form A.

Figure 5:
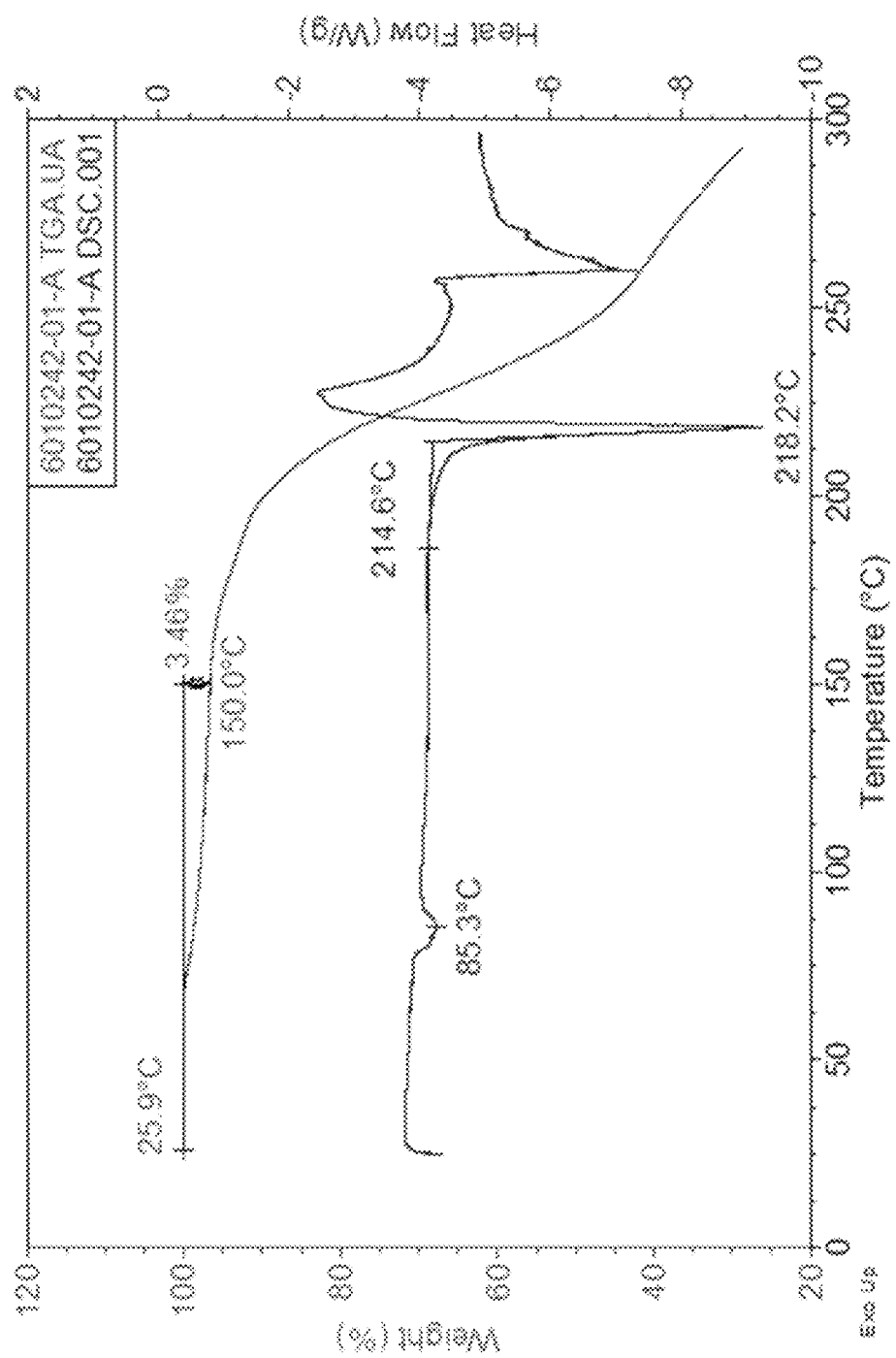
FIG. 5 shows TGA and DSC thermograms of the CV-8972 starting material.

FIG. 5 shows TGA and DSC thermograms of the CV-8972 starting material. TGA thermogram is shown in green, and DSC thermogram is shown in blue. As shown by the TGA and DSC data, about 3.46% weight loss was observed up to 150° C. before decomposition. DSC showed a small endotherm at 85.3° C. (peak) and a possible melting endotherm at 214.6° C. (onset), followed by decomposition. and a melting point at 131.7° C. (peak) was observed.

Figure 6:
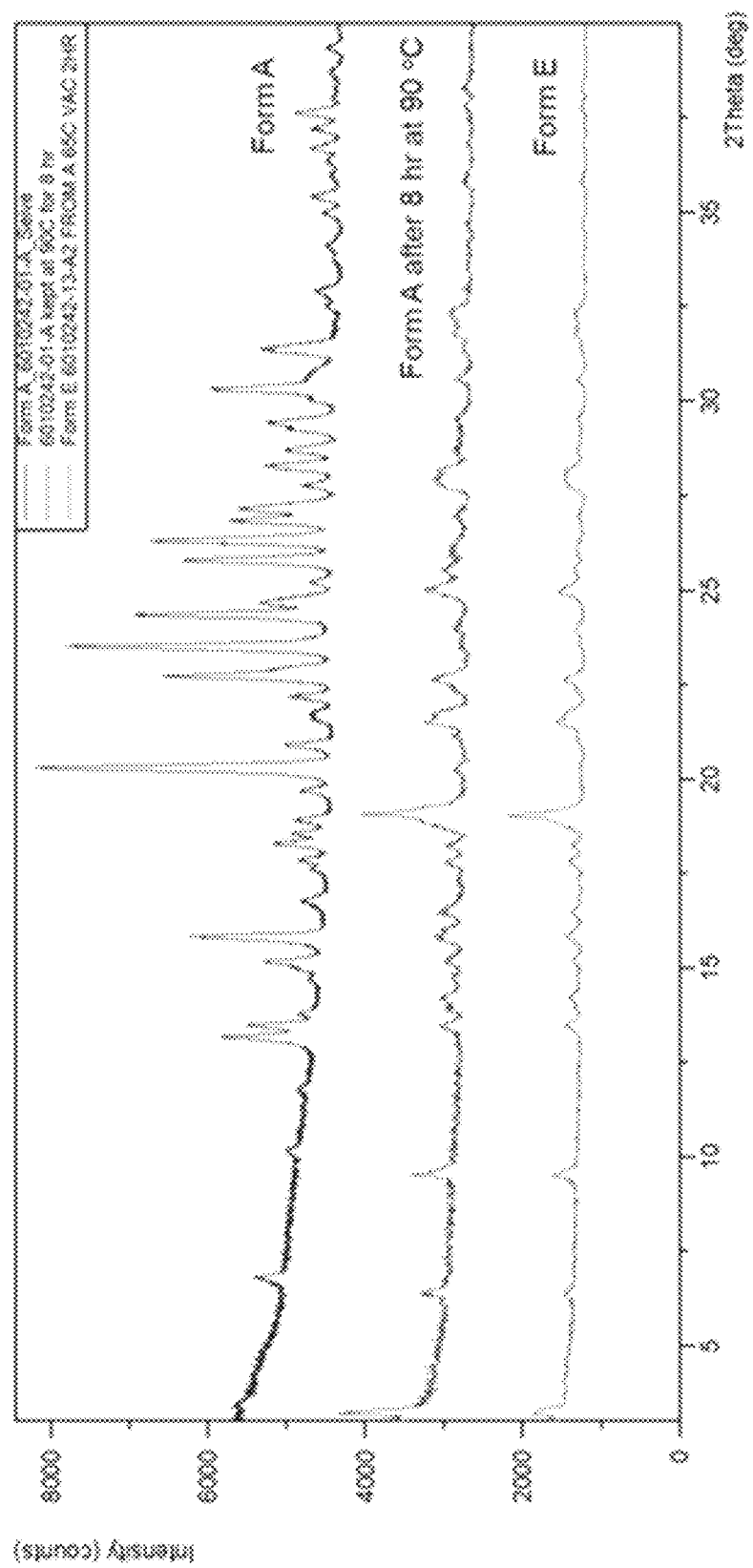
FIG. 6 shows XRPD diffractograms of various forms of CV-8972.

FIG. 6 shows XRPD diffractograms of various forms of CV-8972. CV-8972 starting material is shown in blue; CV-8972 following incubation at 90° C. for 8 hours is shown in red; and CV-8972 following incubation at 65° C. in a vacuum for 2 hours is shown in purple. To see if the small DSC endotherm at 85.3° C. corresponds to polymorphic phase transition or dehydration, XRPD was performed on Form A after storing it in an oven at 90° C. for 8 hours. The data showed that the Form A converts to Form E.

Figure 7:
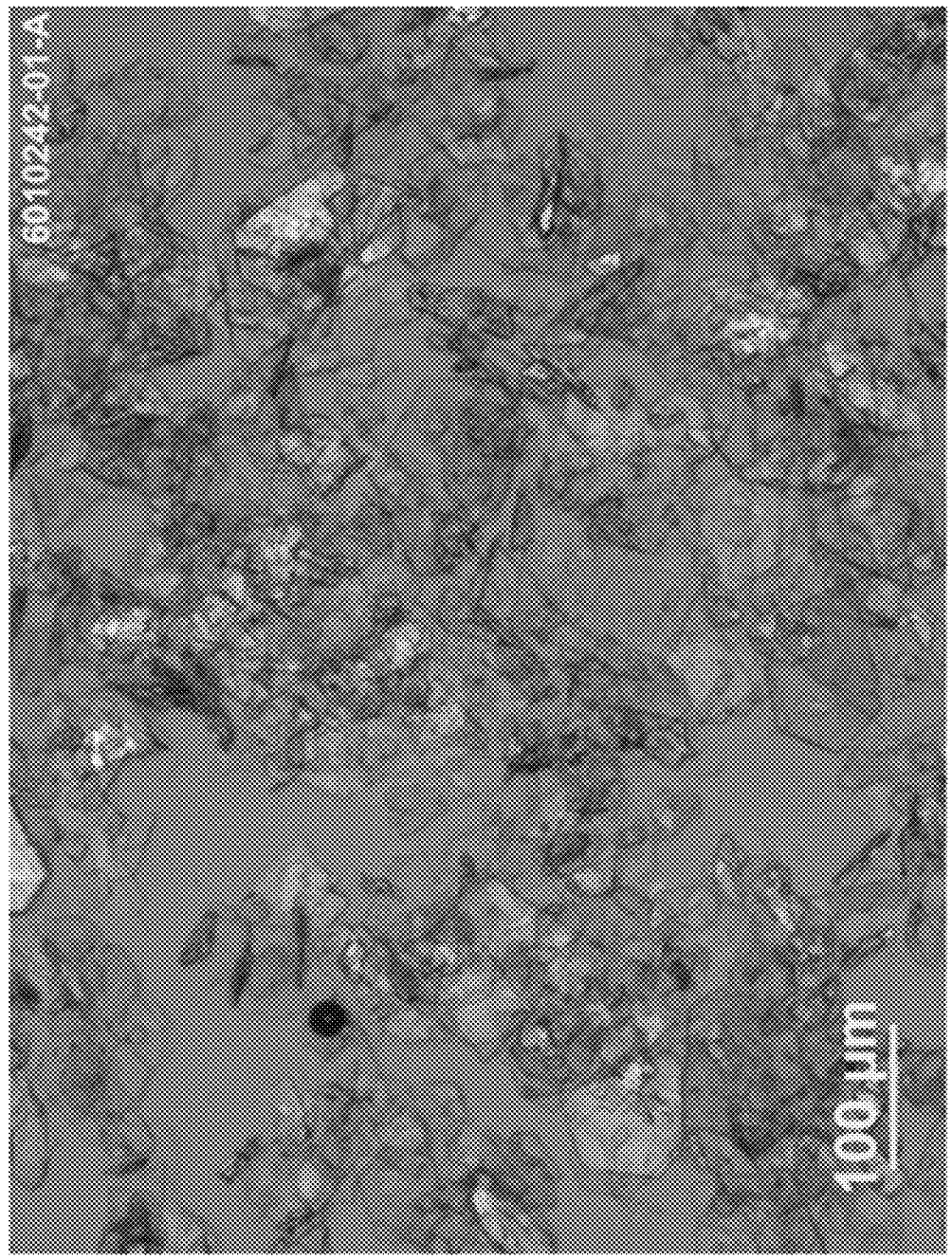
FIG. 7 is a polarized microscopic image of CV-8972 starting material.

FIG. 7 is a polarized microscopic image of CV-8972 starting material. Very platy "mica-like" morphology of the crystals was observed by PLM.

Figure 8:
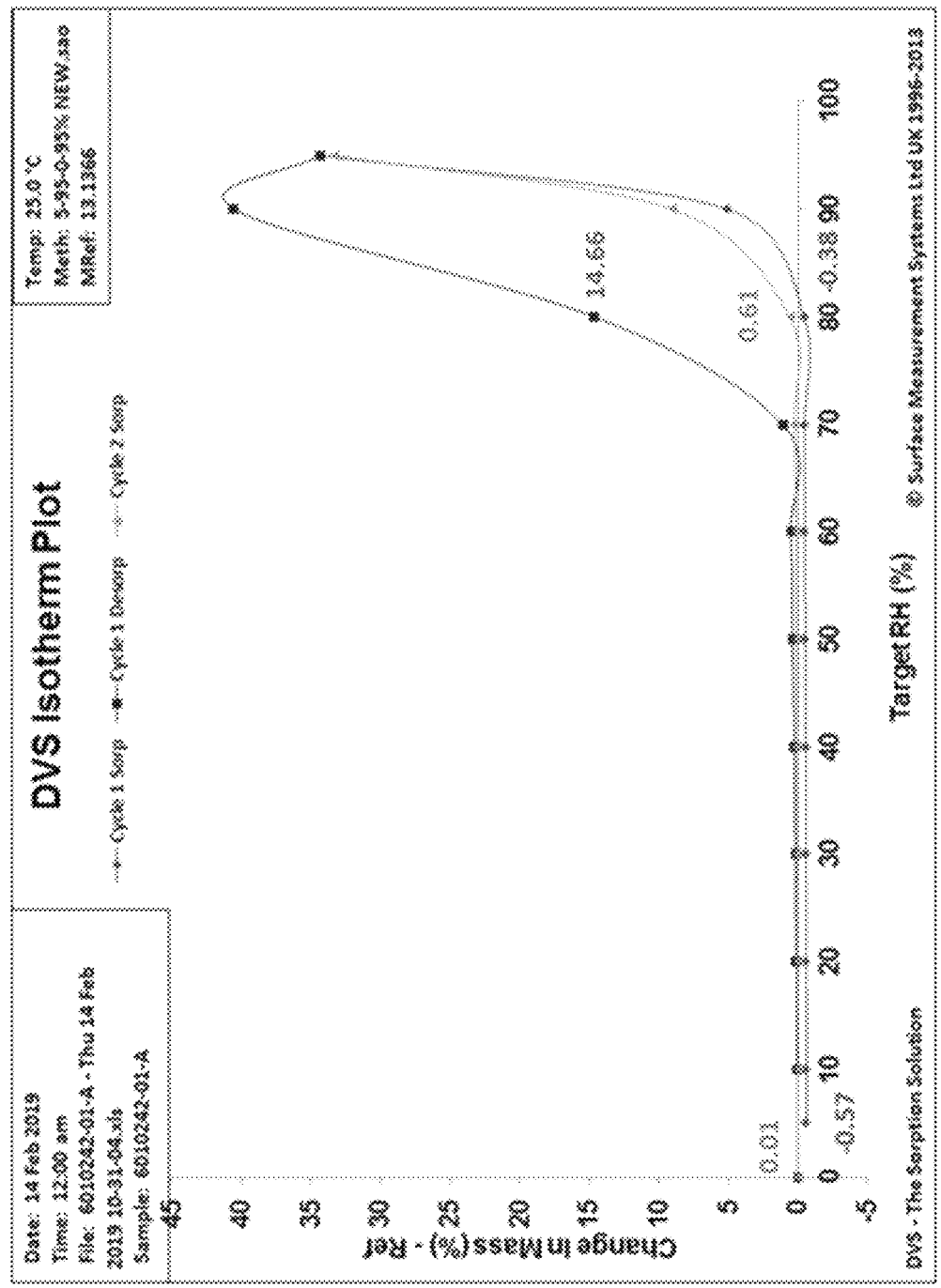
FIG. 8 is a dynamic vapor sorption isotherm plot.

FIG. 8 is a dynamic vapor sorption isotherm plot. Cycle sorption is shown in red; cycle 1 desorption is shown in blue; and cycle 2 sorption is shown in green. DVS results showed that water uptake of CV-8972 is <0.2% at 25° C. and 80% relative humidity (RH) indicated that starting material was non hygroscopic. However, there is a drastic increase in the mass change beyond 80% RH, which indicates there could be deliquescence.

Figure 9:
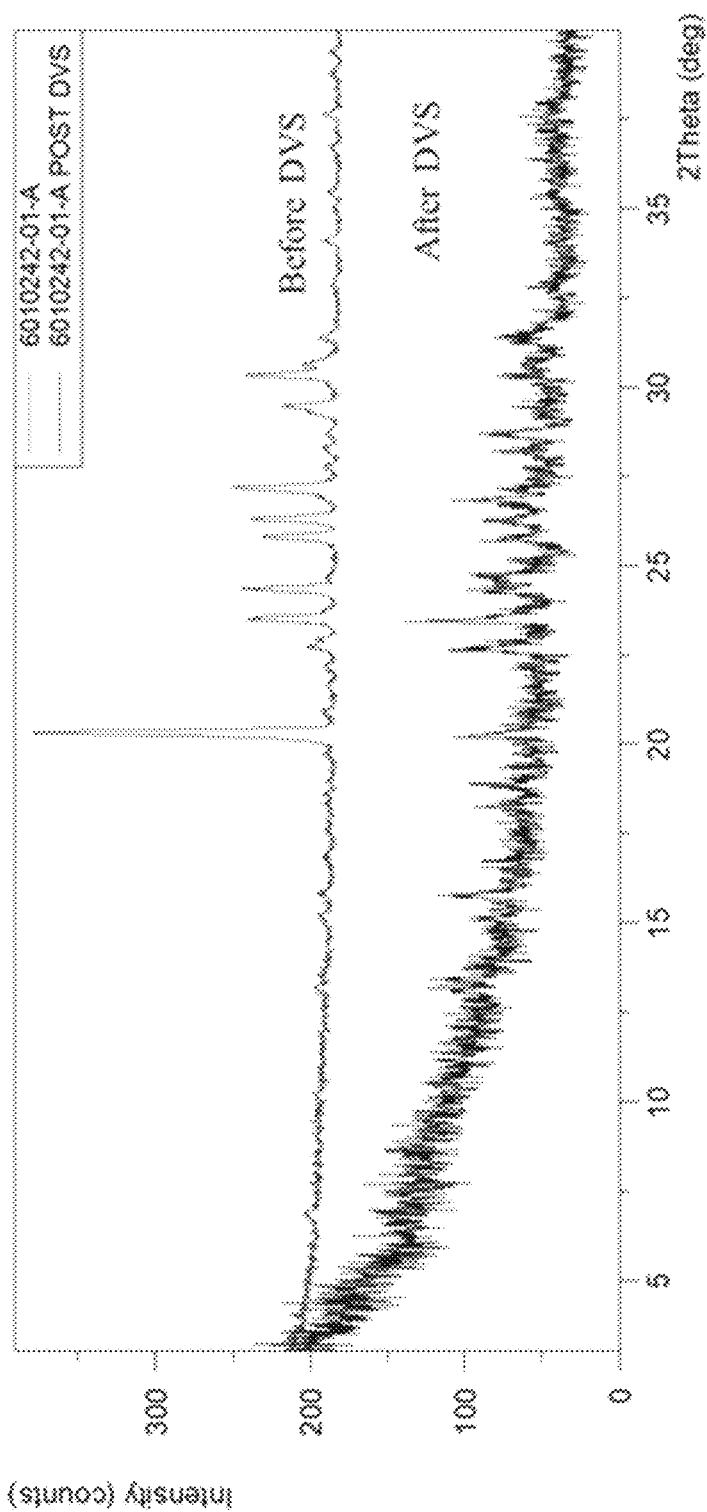
FIG. 9 shows XRPD diffractograms of CV-8972 before and after dynamic vapor sorption.

FIG. 9 shows XRPD diffractograms of CV-8972 before and after dynamic vapor sorption. Pre-DVS data is shown in red; and post-DVS data is shown in blue. The XRPD of the sample after DVS indicated weak crystalline peaks but was mostly similar to the starting material.

Figure 10:
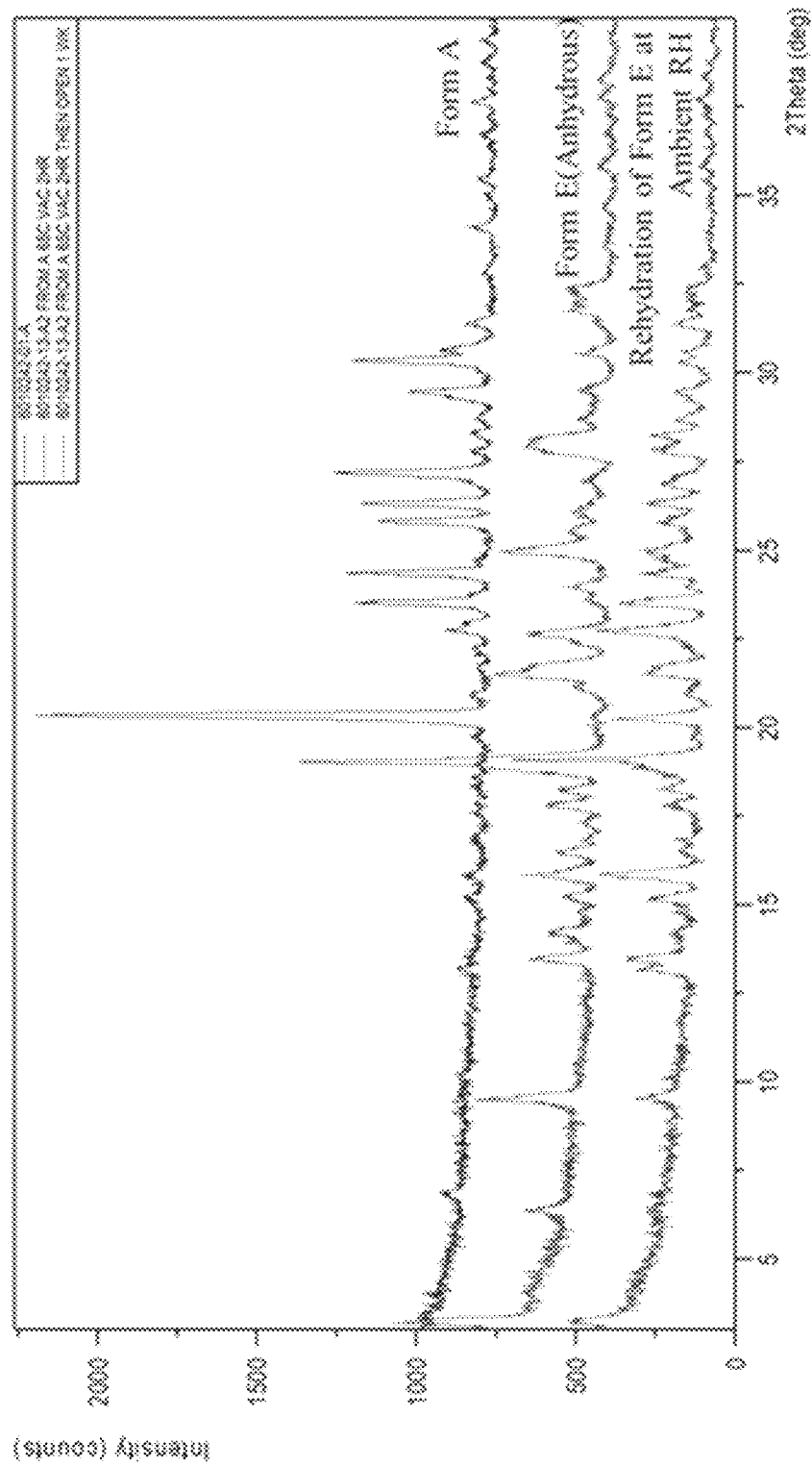
FIG. 10 shows XRPD diffractograms of CV-8972 in its dehydrated and rehydrated forms.

FIG. 10 shows XRPD diffractograms of CV-8972 in its dehydrated and rehydrated forms. Data from starting material is shown in blue; data following incubation for 2 hours in vacuum oven are shown in red; and data from heated material that was exposed to ambient relative humidity is shown in green. To monitor Form A in its dehydrated state, it was placed in a vacuum oven at 65° C. for 2 hours followed by its XRPD analysis. The XRPD results showed that this process created a new anhydrous form of the material and assigned as Form E. Rehydration of Form E when exposed to ambient RH resulted in its partial conversion to Form A.

X-ray powder diffraction data has been challenging to interpret due to the extreme preferred orientation, which results in large variations in the peak intensities from one sample preparation to the next. To minimize this effect, single crystal X-ray diffraction was used to acquire the crystallographic structure, and the X-ray powder diffraction that should be observed in an ideal sample that is absent of preferred orientation was calculated.

Polymorph/Single Crystal Screening

Starting with Form A, polymorph screening experiments were set up under 34 conditions using methods of slurry conversion, liquid vapor diffusion, slow evaporation, and slow cooling. The approximate solubility of starting material was determined at room temperature (RT). Accurately weighed samples of approximately 2 mg weight were added into a 3-mL glass vial. Solvents were then added step wise (50/50/200/700 µL) into the vials until the solids were dissolved or a total volume of 1 mL was reached. The solubility of the starting material in various solvents is shown in Table 1.

TABLE 1

Approximate solubility of starting material (6010242-01-A) at RT

| Experiment ID | Solvent (v:v) | Solubility (mg/mL) |
|---|---|---|
| 6010242-02-A1 | n-Heptane | S < 1.9 |
| 6010242-02-A2 | ACN | S < 1.5 |
| 6010242-02-A3 | MIBK | S < 2.0 |
| 6010242-02-A4 | EtOAc | S < 1.8 |
| 6010242-02-A5 | THF | S < 2.2 |
| 6010242-02-A6 | EtOH | S < 1.7 |
| 6010242-02-A7 | Acetone | S < 2.0 |
| 6010242-02-A8 | MEK | S < 2.0 |
| 6010242-02-A9 | IPA | S < 2.3 |
| 6010242-02-A10 | CHCl$_3$ | S < 1.8 |
| 6010242-02-A11 | IPAc | S < 1.7 |
| 6010242-02-A12 | 1,4-Dioxane | S < 1.7 |
| 6010242-02-A13 | CPME | S < 1.5 |
| 6010242-02-A14 | DCM | S < 2.2 |
| 6010242-02-A15 | Toluene | S < 2.3 |
| 6010242-02-A16 | DMSO | 5.0 < S < 15 |
| 6010242-02-A17 | DMF | 1.8 < S < 6.0 |
| 6010242-02-A18 | NMP | 6.7 < S < 20 |
| 6010242-02-A19 | H$_2$O | S > 44.0 |
| 6010242-02-A20 | MeOH | S > 46.0 |

Results from solubility analysis were used to guide the solvent selection in polymorph screening. Polymorph screening experiments were performed using different crystallization or solid transition methods. Polymorph screening experiments are summarized in Table 2.

TABLE 2

| Method | No. of Experiments | Crystal Type |
|---|---|---|
| Liquid vapor diffusion | 24 | Form A, B, C, D, and E |
| Slow evaporation | 2 | Gel |
| Slow cooling | 2 | No precipitation |
| Slurry conversion | 6 | Form A |
| Total | 34 | Form A, B, C, D, and E |

Figure 11:
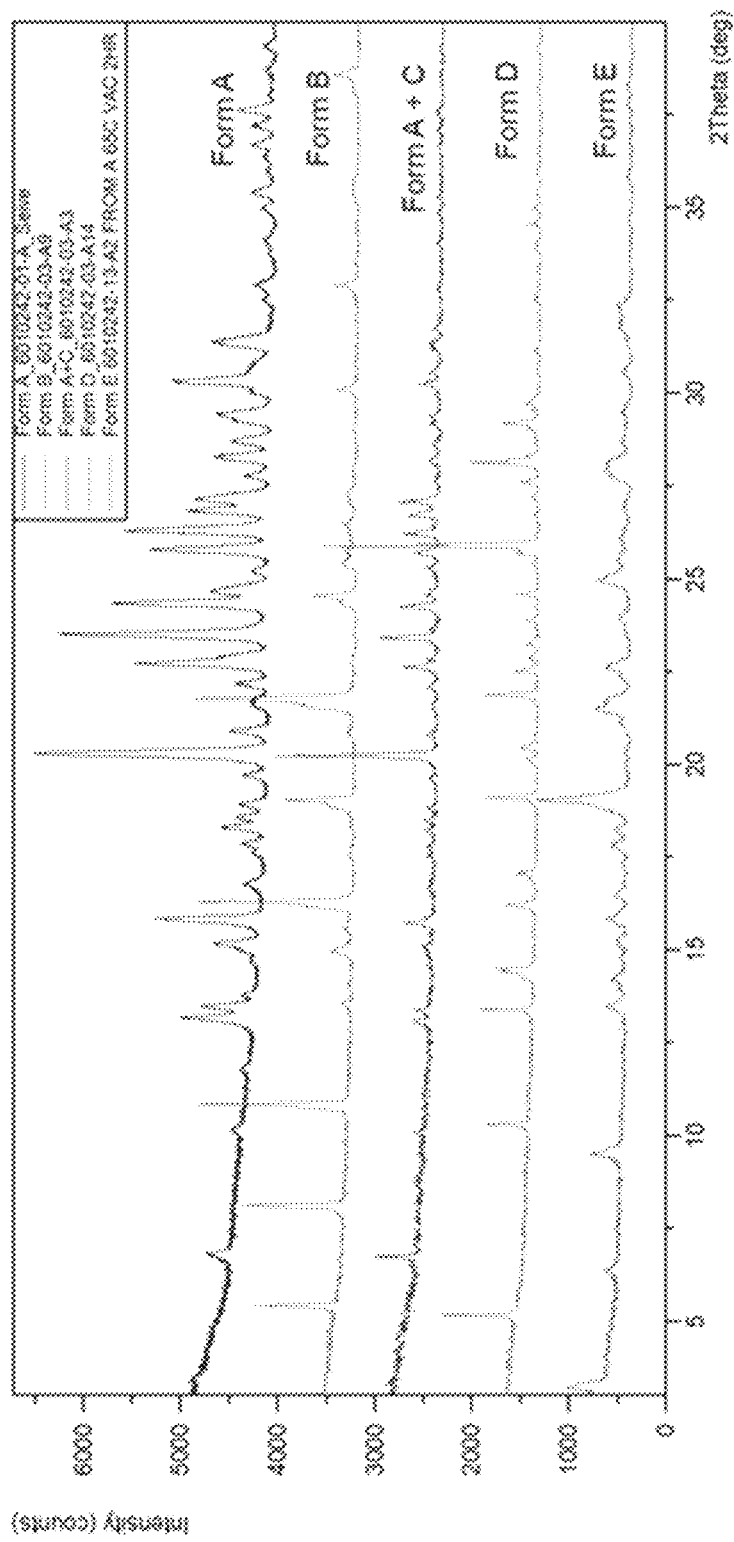
FIG. 11 shows XRPD diffractograms of various polymorphs of CV-8972.

FIG. 11 shows XRPD diffractograms of various polymorphs of CV-8972. Form A is shown in blue; Form B is shown in green; a mixture of Forms A and C is shown in navy; Form D is shown in orange; and Form E is shown in purple.

The various crystal forms of CV-8972 are summarized in Table 3.

TABLE 3

| Crystal Form | Method of obtaining | Form Identification |
|---|---|---|
| Form A | Starting material | Monohydrate* |
| Form B | Liquid vapor diffusion of MTBE in MeOH | Hydrate of unknown stoichiometry[#] |
| Form C (mixed with Form A) | Multiple methods as listed below | Solvate/hydrate |
| Form D | Liquid vapor diffusion of IPA in MeOH | Anhydrate* |
| Form E | 65° C. Vacuum for 2 hours | Anhydrate |

*Single crystal structures for these forms are available and are provided as separate reports
[#]information obtained from separate report Liquid vapor diffusion experiments were conducted in different solvent conditions. Approximately 15-25 mg of starting material was dissolved in an appropriate solvent to obtain a clear solution in a 3-mL vial. This solution was then placed into a 20-mL vial with 3 mL of volatile solvents. The 20-mL vial was sealed with a cap and kept at RT allowing enough time for organic vapor to interact with the solution. The precipitates were isolated for XRPD analysis. Results from liquid vapor diffusion experiments are summarized in Table 4.

TABLE 4

| Experiment ID | Solvent | Anti-solvent | Observation |
|---|---|---|---|
| 6010242-03-A1 | H$_2$O | MEK | Amorphous |
| 6010242-03-A2 | | 1,4-Dioxane | Gel |
| 6010242-03-A3 | | THF | Form A + C |
| 6010242-03-A4 | | Acetone | Form A + C |
| 6010242-03-A5 | | ACN | Form A + C |
| 6010242-03-A6 | | EtOH | Form A + C |
| 6010242-03-A7 | | IPA | Clear |
| 6010242-03-A8 | MeOH | MEK | Form A + C |
| 6010242-03-A9 | | MTBE | Single crystal (Form B) |
| 6010242-03-A10 | | THF | Gel |
| 6010242-03-A11 | | Acetone | Gel |
| 6010242-03-A12 | | ACN | Gel |
| 6010242-03-A13 | | EtOH | Form A + C |
| 6010242-03-A14 | | IPA | Single crystal (Form D) |
| 6010242-03-A15 | | EtOAc | Amorphous solid |
| 6010242-07-A1 | MeOH | IPA | Form E |
| 6010242-07-A2 | | IPA | Form D |
| 6010242-07-A3 | | IPA | Form D |
| 6010242-07-A4 | | Toluene | Form A + C |
| 6010242-07-A5 | | Dioxane | Small single crystal on the wall (Form A + C) |
| 6010242-07-A6 | | MIBK | Small single crystal on the wall (Form A + C) |
| 6010242-04-A1 | H$_2$O | MTBE | Gel |
| 6010242-04-A2 | H$_2$O | IPA | Gel |
| 6010242-04-A3 | MeOH | DCM | Small single crystal on the wall (Form A + C) |

Slow evaporation experiments were performed under various conditions. Briefly, a saturated solution of starting material prepared in different solvents was added to a HPLC vial. The visually clear solutions were covered by Parafilm® with 5~10 pinholes and subjected to evaporation at RT. The solids were isolated for XRPD analysis. Results from slow evaporation experiments are summarized in Table 5.

TABLE 5

| Experiment ID | Solvent (v:v) | Solid Form |
| --- | --- | --- |
| 6010242-06-A1 | MeOH | White solid poor crystalline |
| 6010242-06-A2 | H$_2$O | Gel |

Slow cooling experiments were conducted in two different solvent systems. About 10~15 mg of starting material was suspended in appropriate solvent in a 2-mL glass vial at RT. The suspension was then heated to 50° C., equilibrated for about two hours and filtered using a nylon membrane (pore size of 0.22 μm). Each filtrate was slowly cooled down to 5° C. at a rate of 0.1° C./min. Results from slow cooling experiments are summarized in Table 6.

TABLE 6

| Experiment ID | Solvent (v:v) | Solid Form |
| --- | --- | --- |
| 6010242-05-A1 | DMSO | No precipitation |
| 6010242-05-A2 | NMP | No precipitation |

Slurry conversion experiments were conducted at RT in different solvent systems. Approximately 20 mg of starting material was suspended in 0.1 mL of solvent in HPLC vials. After the suspension was stirred magnetically for 48 hours at RT, the remaining solids were isolated for XRPD analysis. Results from slurry conversion experiments are summarized in Table 7.

TABLE 32

| Experiment ID | Solvent (v:v) | Solid Form |
| --- | --- | --- |
| 6010242-15-A1 | Acetone | Form A |
| 6010242-15-A2 | Acetone/H$_2$O (a$_w$ = 0.2, 941/59) | Form A |
| 6010242-15-A3 | Acetone/H$_2$O (a$_w$ = 0.4, 857/143) | Form A |
| 6010242-15-A4 | Acetone/H$_2$O (a$_w$ = 0.6, 726/274) | Form A |
| 6010242-15-A5 | Acetone/H$_2$O (a$_w$ = 0.8, 492/508) | Form A |
| 6010242-15-A6 | H$_2$O | Form A |
| 6010242-15-A7 | Form D + E in acetone | Form A |

CONCLUSIONS

The Form A was successfully characterized to understand its form behavior. A comprehensive polymorph screening in 34 different conditions was performed. Five polymorph of the CV-8972 were identified during the screening, including Form A, Form B, a mixture of Forms A+C, Form D, and Form E. Form D and E are anhydrous, Form A is a monohydrate, and Form B is a hydrate with unknown stoichiometry. Phase origin of Form C is not known since it was not obtained it in pure form; it always crystallized as mixture with Form A. Based on polymorph screening it is apparent that CV-8972 has a tendency to form multiple polymorphs. Current studies have concluded that Form A is the best form for development of CV-8972 and is a stable monohydrate form, and is the most stable form under conditions of ambient temperature and humidity.

Instruments and Methods

Starting material was used to analyze Form A and screen for other polymorphs.

XRPD was performed with a Panalytical X'Pert3 Powder XRPD on a Si zero-background holder. The 2θ position was calibrated against a Panalytical Si reference standard disc. Instrumental parameters used for XPRD are listed in Table 8.

TABLE 8

| Parameters | Reflection Mode |
| --- | --- |
| X-Ray wavelength | Cu, kα |
| | Kα1 (Å): 1.540598, |
| | Kα2 (Å): 1.544426, |
| | Kα2/Kα1 intensity ratio: 0.50 |
| X-Ray tube setting | 45 kV, 40 mA |
| Divergence slit | Fixed 1/8° |
| Scan mode | Continuous |
| Scan range (° 2TH) | 3-40 |
| Scan step time [s] | 18.87 |
| Step size (° 2TH) | 0.0131 |
| Test Time | 4 min 15 s |

TGA data was collected using a TA Discovery 550 TGA from TA Instrument. DSC was performed using a TA Q2000 DSC from TA Instrument. DSC was calibrated with Indium reference standard and the TGA was calibrated using nickel reference standard. Detailed parameters used for TGA and DSC are listed in Table 9.

TABLE 9

| Parameters | TGA | DSC |
| --- | --- | --- |
| Method | Ramp | Ramp |
| Sample pan | Platinum, open | Aluminum, crimped |
| Temperature | | RT - 300° C. |
| Heating rate | | 10° C./min |
| Purge gas | | N$_2$ |

Polarized light microscopic (PLM) pictures were captured on a Nikon DS-Fi2 upright microscope at room temperature. Low viscosity microscope immersion oil (Resolve®) was used to disperse powder crystals.

Example 2

Summary

To determine the crystal structure of CV-8972, a single monohydrate crystal was grown, and a suitable single crystal was used for a full crystal X-ray diffraction (SCXRD) data collection at 199 K. A crystal structure with a R$_1$ value of 0.0303 (I>2σ(I)) was obtained. The structure showed that this crystal form is a monohydrate, tri-HCl salt.

Crystal Growth and SCXRD Preparation

Single crystals of C$_{22}$H$_{34}$Cl$_3$N$_3$O$_6$ (CV-8972) were obtained via slow cooling: 163.2 mg starting material was weighed into a 2-mL glass vial, and 0.100 mL water was added to dissolve the solids at 50° C., then the solution was slowly cooled to 10° C. over 12 hours before harvesting.

Figure 12:
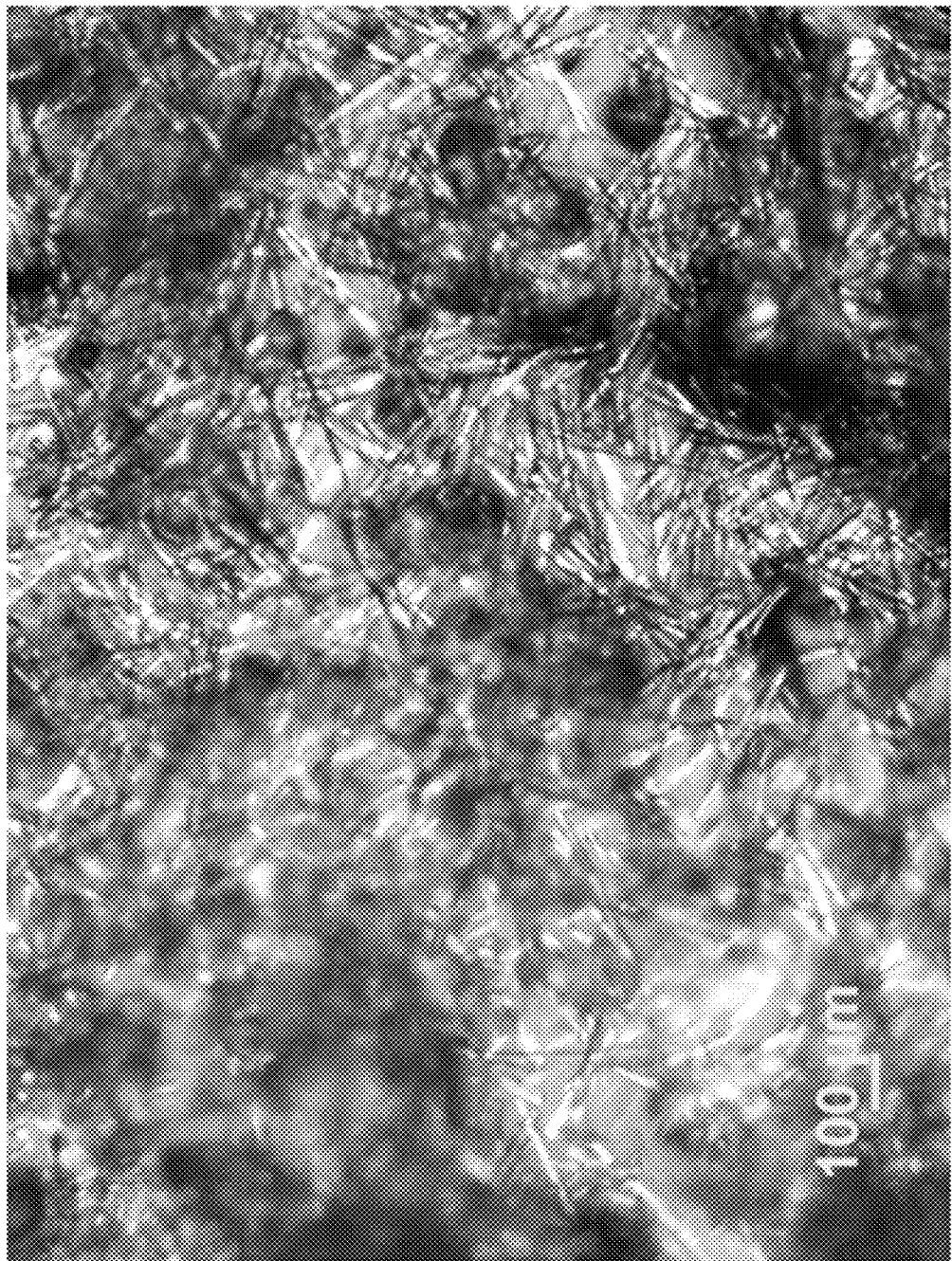
FIG. 12 is a PLM image of a batch of single crystals of $C_{22}H_{34}Cl_3N_3O_6$ (CV-8972).

FIG. 12 is a PLM image of a batch of single crystals of C$_{22}$H$_{34}$Cl$_3$N$_3$O$_6$ (CV-8972). Bar represents 100 μm.

Figure 13:
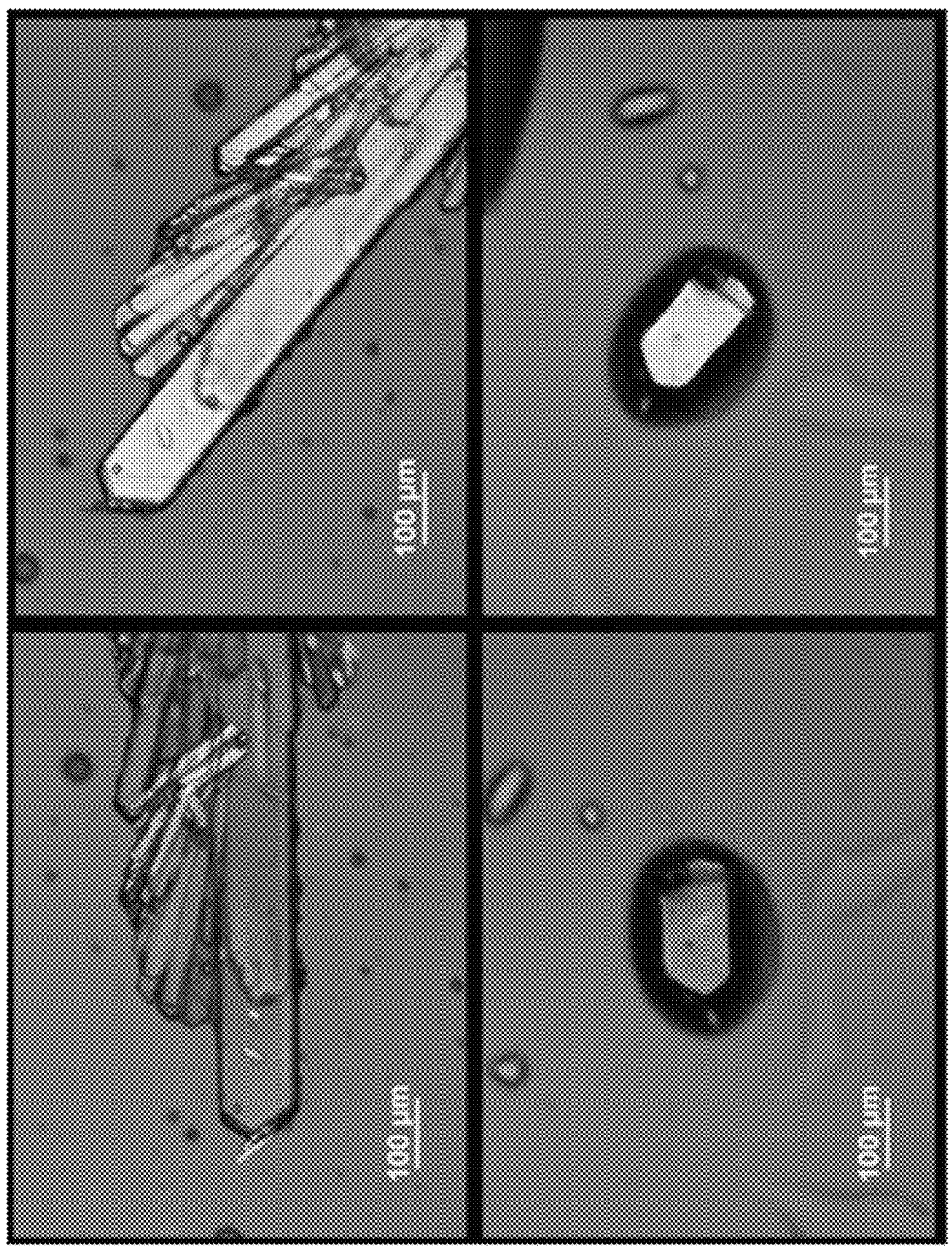
FIG. 13 shows PLM images of a crystal used for single-crystal diffractometer.

FIG. 13 shows PLM images of a crystal used for single-crystal diffractometer. Bars represent 100 μm. A thick needle was picked out and trimmed down to a size of 200×160×100 μm uniform block. This sample was mounted on a 100 mm MiTeGen MicroLoop™ with low viscosity cryo-oil (MiTeGen LV CryoOil™).

Figure 14:
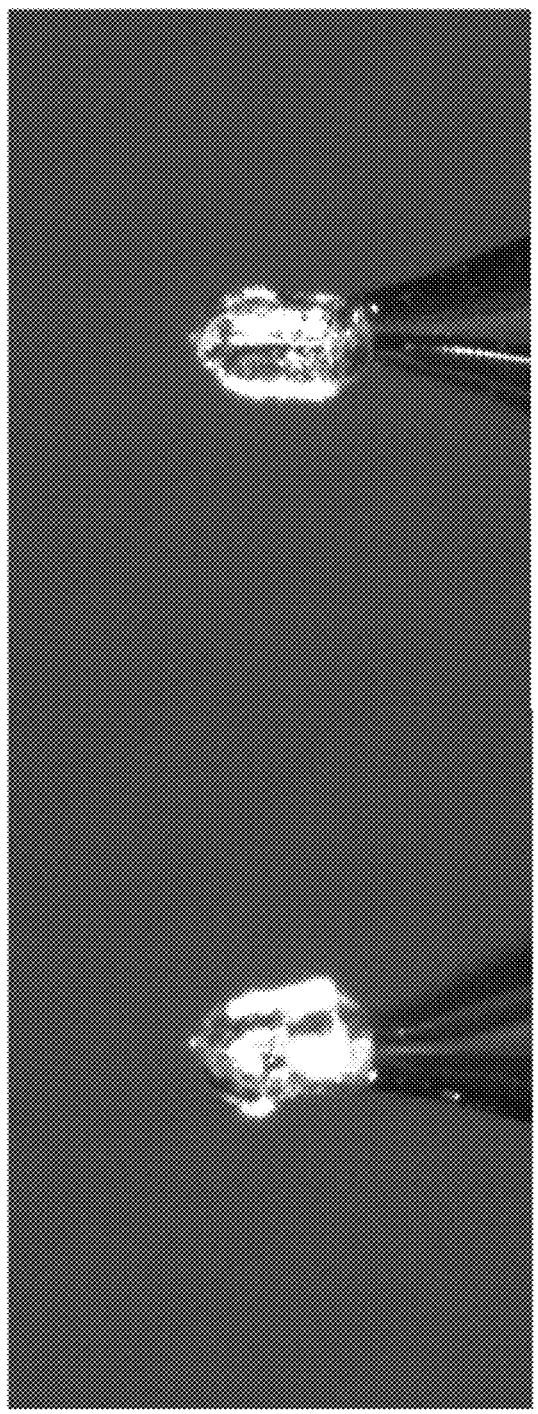
FIG. 14 shows images of a crystal mounted on a 100 micro Mitegen loop on the diffractometer.

FIG. 14 shows images of a crystal mounted on a 100 micro Mitegen loop on the diffractometer.

Single Crystal Structure Determination

A total of 9576 frames were collected using Bruker Apex3 v2018-7.2. The total exposure time was 18 hours (exposure times were adjusted based on 2θ). The frames were integrated with the Bruker SAINT software package using a narrow-frame algorithm. The integration of the data using an orthorhombic unit cell yielded a total of 157237 reflections to a maximum θ angle of 81.01° (0.78 Å resolution), of which 5641 were independent (average redundancy 27.874, completeness=99.8%, $R_{int}$=4.41%, $R_{sig}$=1.34%) and 5388 (95.51%) were greater than 2σ($F^2$). The final cell constants of a=7.8826(2) Å, b=12.4776(3) Å, c=52.3580(13) Å, volume=5149.7(2) Å$^3$, are based upon the refinement of the XYZ-centroids of 1406 reflections above 20 σ(I) with 11.75°<2θ<100.6°. Data were corrected for absorption effects using the Multi-Scan method (SADABS). The ratio of minimum to maximum apparent transmission was 0.788. The calculated minimum and maximum transmission coefficients (based on crystal size) are 0.5340 and 0.7160.

The structure was solved and refined using the Olex2 incorporating SHELXTL Software Package using the orthorhombic space group Pbca, with Z=8 for the formula unit, $C_{22}H_{34}Cl_3N_3O_6$. One asymmetric unit contains one whole API molecule. The final anisotropic full-matrix least-squares refinement on $F^2$ with 330 variables (0 restraints) converged at $R_1$=3.03%, for the observed data and wR2=7.98% for all data. The goodness-of-fit was 1.041. The largest peak in the final difference electron density synthesis was 0.358 e–/Å3 (0.81 Å from $Cl_1$) and the largest hole was –0.438 e–/Å3 (0.66 Å from $Cl_1$). Most of the positions and thermal ellipsoids of hydrogens were treated as riding models (AFIX 23, AFIX 43, and AFIX 137 used). However, the crucial hydrogen atoms involving hydrogen bonding and salt formation were refined freely without any constraints. On the basis of the final model, the calculated density was 1.400 g/cm$^3$ and F(000), 2288 e–. Crystallographic parameters of the $C_{22}H_{34}Cl_3N_3O_6$ crystal are summarized in Table 10.

TABLE 10

| Identification code | 6010242_13 |
|---|---|
| Chemical formula | $C_{22}H_{34}Cl_3N_3O_6$ |
| Formula weight | 542.87 g/mol |
| Wavelength | 1.54178 Å |
| Temperature | 199.0 K |
| Crystal size | 0.10 × 0.16 × 0.20 mm |
| Crystal habit | colorless trimmed needle |
| Crystal system | orthorhombic |
| Space group | Pbca |
| Unit cell dimensions | a = 7.8826(2) Å    α = 90° |
|  | b = 12.4776(3) Å    β = 90° |
|  | c = 52.3580(13) Å    γ = 90° |
| Volume | 5149.7(2) Å$^3$ |
| Z | 8 |
| Density (calculated) | 1.400 g/cm$^3$ |
| Absorption coefficient(μ(CuKα)) | 3.583 mm$^{-1}$ |
| F(000) | 2288 |
| Theta range for data collection | 3.38 to 81.01° |
| Index ranges | –10 <= h <= 10, –15 <= k <= 15, – 66 <= l <= 66 |
| Reflections collected | 157237 |
| Independent reflections | 5641 [R(int) = 0.0441] |
| Coverage of independent reflections | 99.8% |
| Absorption correction | Multi-Scan |
| Max. and min. transmission | 0.7160 and 0.5340 |
| Structure solution technique | direct methods |
| Structure solution program | XS (Sheldrick, 2008) |
| Refinement method | Full-matrix least-squares on $F^2$ |
| Refinement program | XL (Sheldrick, 2008) |
| Function minimized | $\Sigma w(F_o^2 - F_c^2)^2$ |
| Data/restraints /parameters | 5641/0/330 |
| Goodness-of-fit on $F^2$ | 1.041 |
| Δ/σ$_{max}$ | 0.001 |
| Final R indices | 5388 data; I > 2σ(I) |
|  | $R_1$ = 0.0303, wR2 = 0.0783 |
|  | all data |
|  | $R_1$ = 0.0318, wR2 = 0.0798 |

TABLE 10-continued

| Weighting scheme | w = 1/[σ$^2$($F_o^2$) + (0.0364P)$^2$ + 2.7627P] where P = ($F_o^2$ + 2$F_c^2$)/3 |
|---|---|
| Largest diff. peak and hole | 0.358 and –0.438 eÅ$^{-3}$ |
| R.M.S. deviation from mean | 0.045 eÅ$^{-3}$ |

Figure 15:
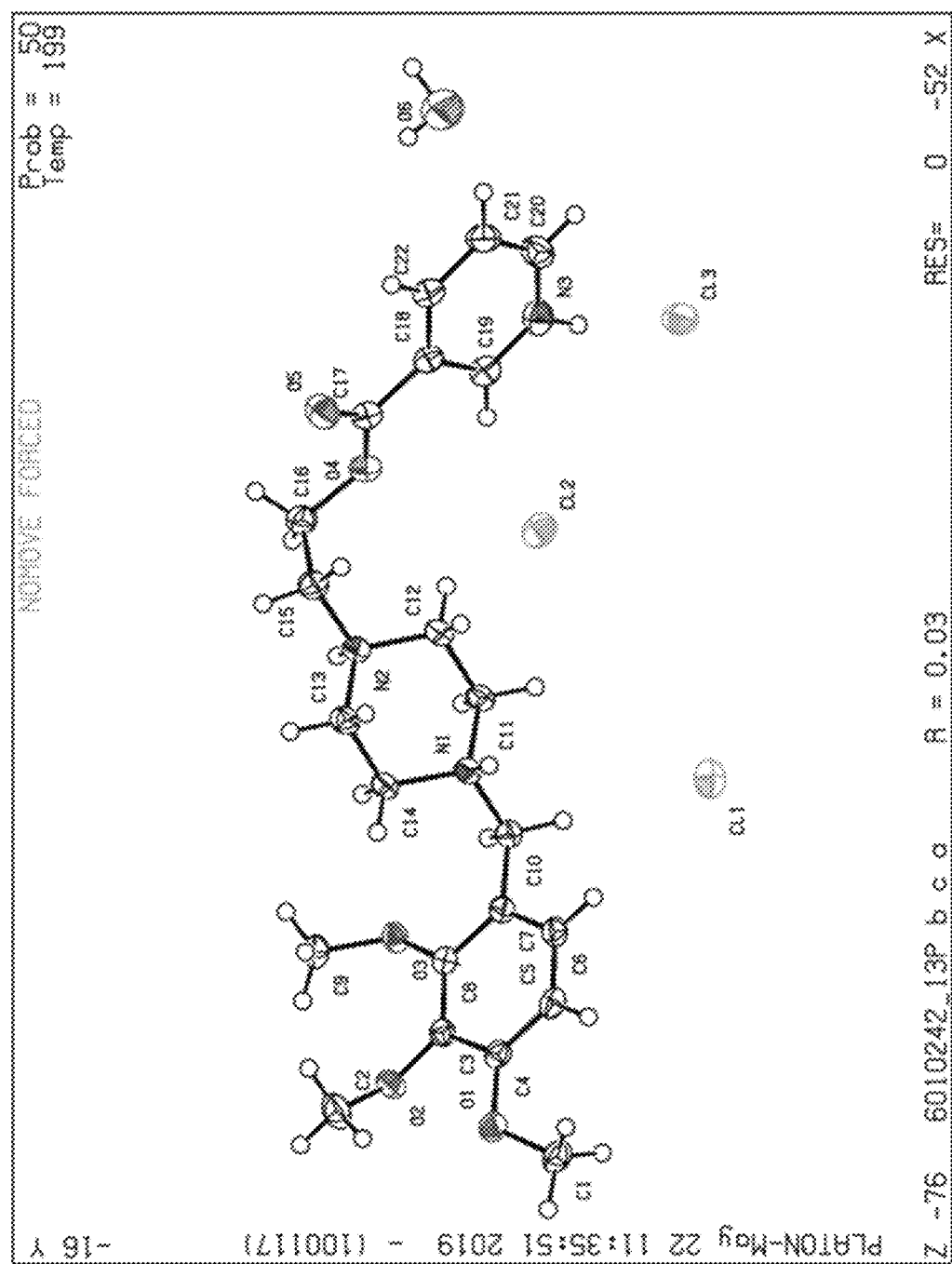
FIG. 15 is an Ortep diagram of an asymmetric unit of the $C_{22}H_{34}Cl_3N_3O_6$ crystal.

FIG. 15 is an Ortep diagram of an asymmetric unit of the $C_{22}H_{34}Cl_3N_3O_6$ crystal. The Ortep diagram of an asymmetric unit of the $C_{22}H_{34}Cl_3N_3O_6$ crystal demonstrates that this API is a monohydrate tris-HCl salt, as a ratio of 1:3:1 (API:HCl:H$_2$O) was observed.

Figure 16:
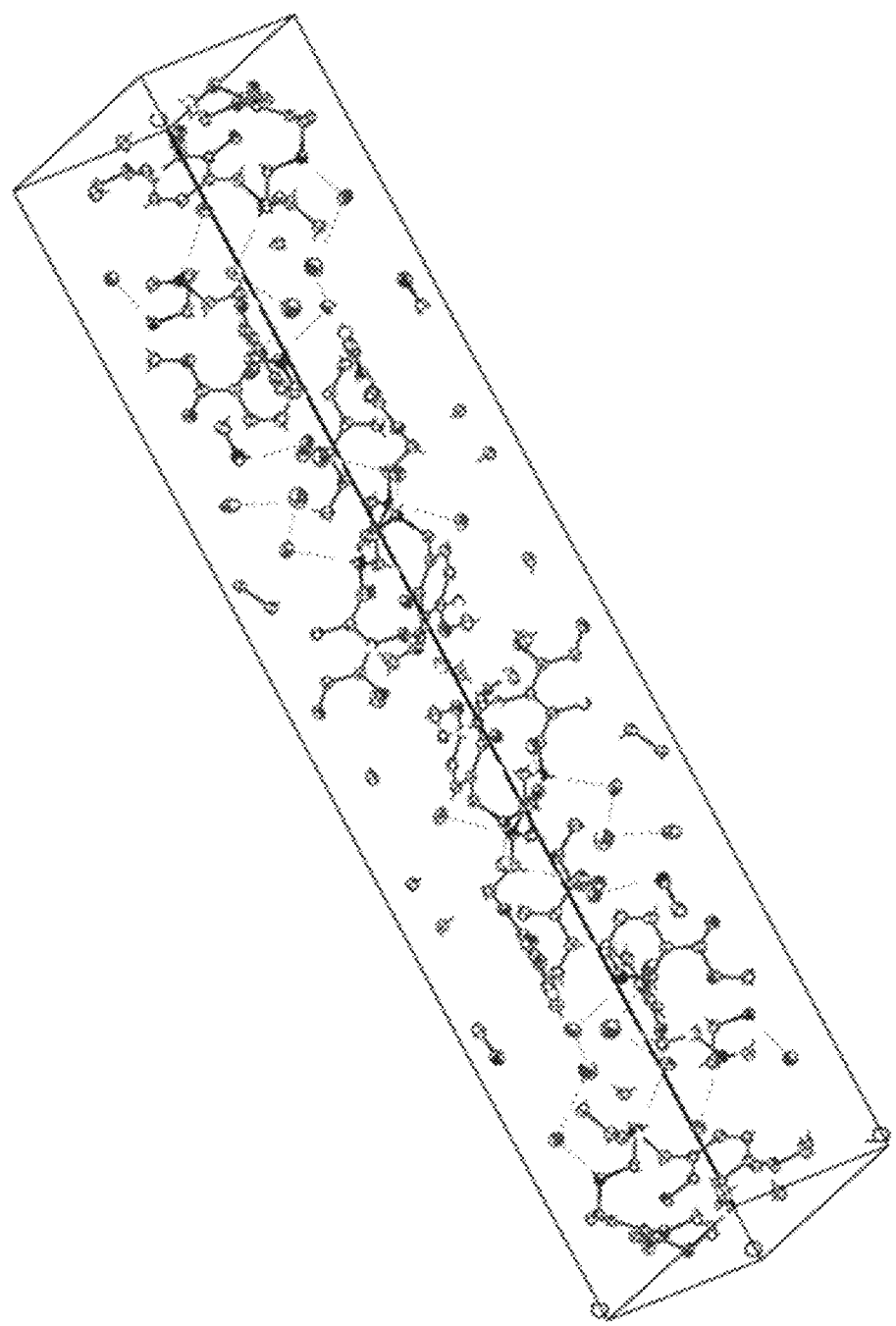
FIG. 16 shows one unit cell of the $C_{22}H_{34}Cl_3N_3O_6$ crystal.

FIG. 16 shows one unit cell of the $C_{22}H_{34}Cl_3N_3O_6$ crystal.

Figure 17:
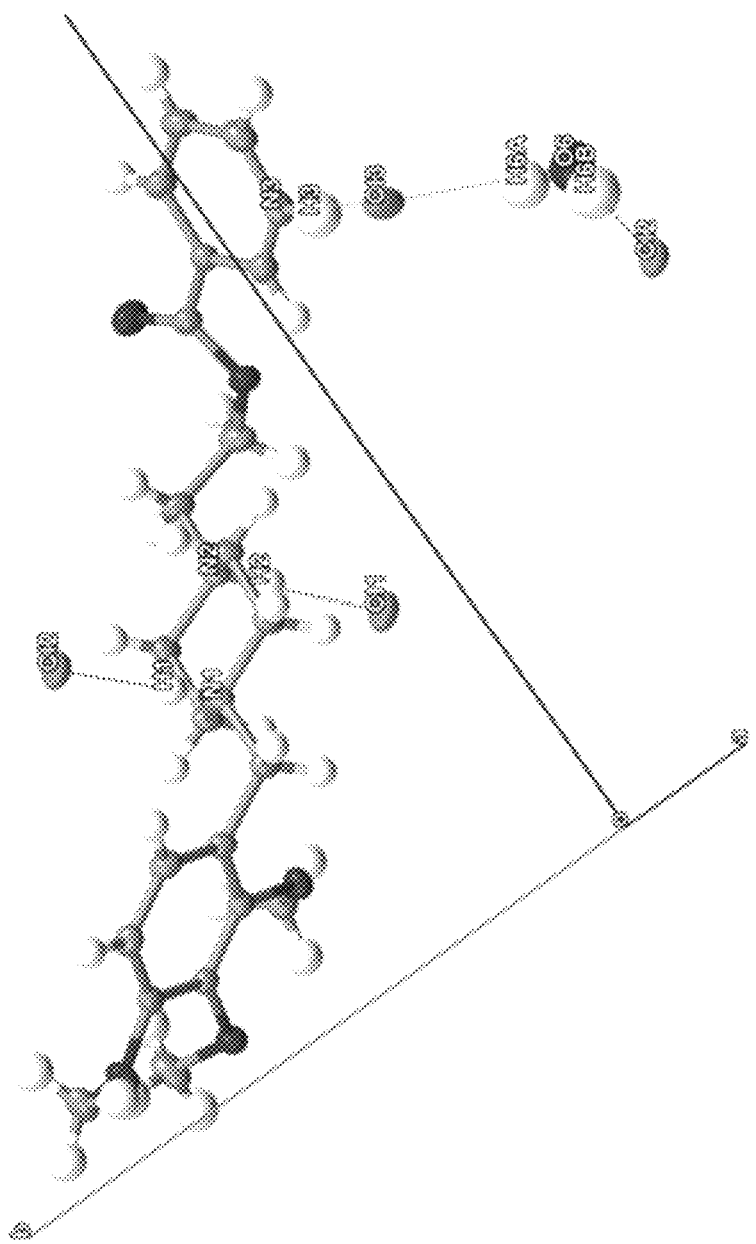
FIG. 17 is a diagram of hydrogen bonds networks and counter-ion pairs in the $C_{22}H_{34}Cl_3N_3O_6$ crystal.

FIG. 17 is a diagram of hydrogen bonds networks and counter-ion pairs in the $C_{22}H_{34}Cl_3N_3O_6$ crystal. The diagram shows that the three hydrochloride molecules are deprotonated, whereas the three nitrogens are protonated. The water molecule serves as a hydrogen bond donor to bridging two chlorine anions. The crystallographic measurements of the hydrogen bonds and counter-ion pairs in the $C_{22}H_{34}Cl_3N_3O_6$ crystal are summarized in Table 11.

TABLE 11

| D-H ... A | d(D ... A)/Å | (D-H ... A)/° | d(D ... A) | <(DHA) |
|---|---|---|---|---|
| O6-H6A ... Cl3$^{\#1}$ | 0.85(3) | 2.37(3) | 3.1997(18) | 167.(2) |
| O6-H6B ... Cl2$^{\#2}$ | 0.91(3) | 2.27(3) | 3.1815(16) | 176.(2) |
| N2-H2 ... Cl1$^{\#3}$ | 0.932(18) | 2.119(18) | 3.0499(11) | 177.1(16) |
| N1-H1 ... Cl2$^{\#4}$ | 0.919(17) | 2.127(18) | 3.0462(11) | 179.2(16) |
| N3-H3 ... Cl3 | 0.95(2) | 2.07(2) | 2.9891(13) | 163.9(19) |

Symmetry transformations used to generate equivalent atoms: #1: 2 – X, 0.5 + Y, 0.5 – Z; #2: 0.5 + X, +Y, 0.5 – Z; #3: 1 + X, +Y,+Z; $4: 1.5 – X, 0.5 + Y, +Z The final cif file was checked with Platon using Olex2 locally, only one level C alert was found (missing three reflections), together with eight level G alerts. An extensive data collection strategy was implemented to prevent this issue, and the completeness and redundancy of this dataset were 99.8% and 27.87, respectively.

Figure 18:
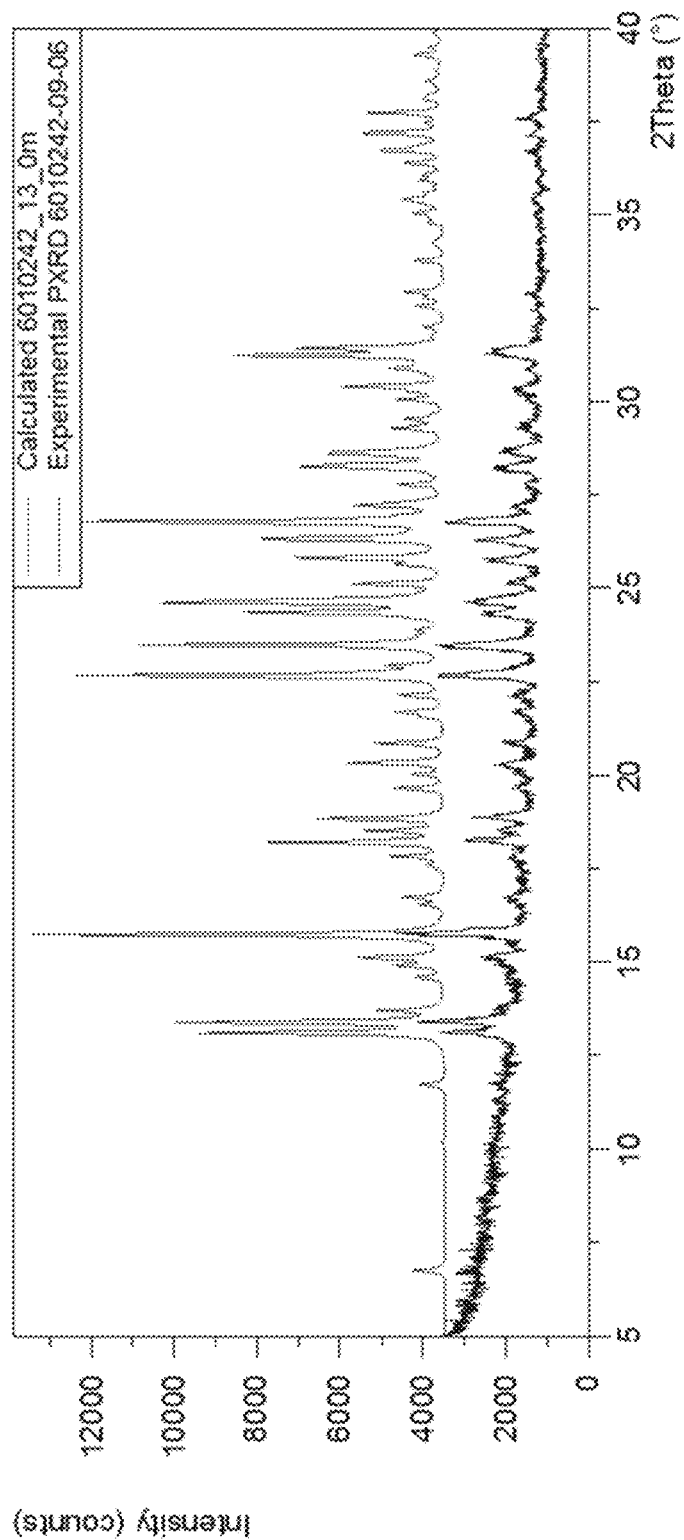
FIG. 18 shows calculated and measured XRPD diagrams of the $C_{22}H_{34}Cl_3N_3O_6$ crystal.

FIG. 18 shows calculated and measured XRPD diagrams of the $C_{22}H_{34}Cl_3N_3O_6$ crystal. Calculated XRPD diffractogram is shown in red; and measured XRPD diffractogram is shown in blue. Powder x-ray diffraction of this batch was obtained and compared with a calculated pattern based on this crystal structure using Mercury. The experimental peak positions and intensities fit well with the calculated pattern.

Instruments and Methods

The X-ray intensity data were measured at 199.0 K (controlled by Oxford Cryostream 800) on a Bruker Venture X-ray diffractometer. Incoatec Microfocus Source (IμS 3.0) monochromated Cu Kα radiation (λ=1.54178 Å, voltage=50 kV, current=1.1 mA) was used as the x-ray source. The intensity data was collected by a Photon II detector.

Polarized light microscopic picture was captured on Nikon DS-Fi2 upright microscope at room temperature.

XRPD was performed with a Panalytical X'Pert3 Powder XRPD on a Si zero-background holder. The 2θ position was calibrated against a Panalytical Si reference standard disc.

Example 3

Summary

To determine the crystal structure of CV-8972, a single anhydrate crystal of CV-8972 was grown, and a suitable single crystal was used for a full SCXRD data collection at 102 K. A crystal structure with a $R_1$ value of 0.0328 (I>2σ(I)) was obtained. The structure showed that this crystal form is an anhydrous tri-HCl salt.

Crystal Growth and SCXRD Preparation

Single crystals of anhydrous tri-HCl salt of CV-8972 were obtained via liquid vapor diffusion of MTBE in MeOH solution. Briefly, a saturated solution of CV-8972 in MeOH was obtained at RT and filled into 2-mL glass vial, which was then kept inside a bigger 20 mL vial having 2 mL of MTBE. The vial was taken out when it showed presence of white crystalline material.

Figure 19:
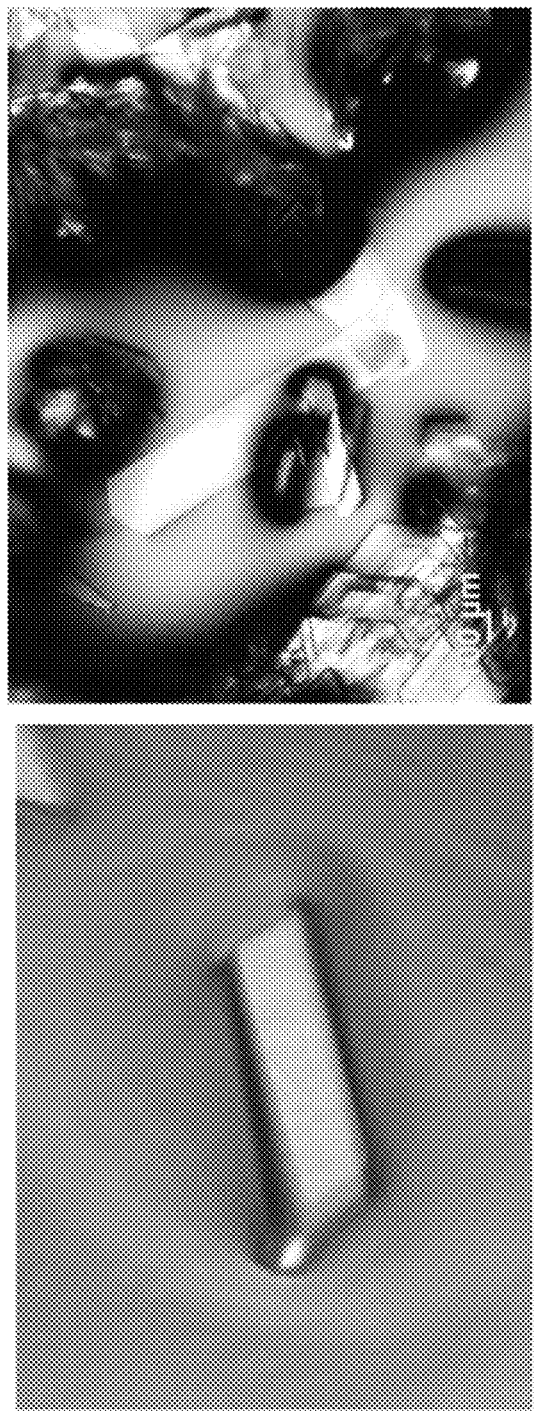
FIG. 19 shows PLM images of single anhydrous crystals from recrystallized CV-8972.

FIG. 19 shows PLM images of single anhydrous crystals from recrystallized CV-8972.

Figure 20:
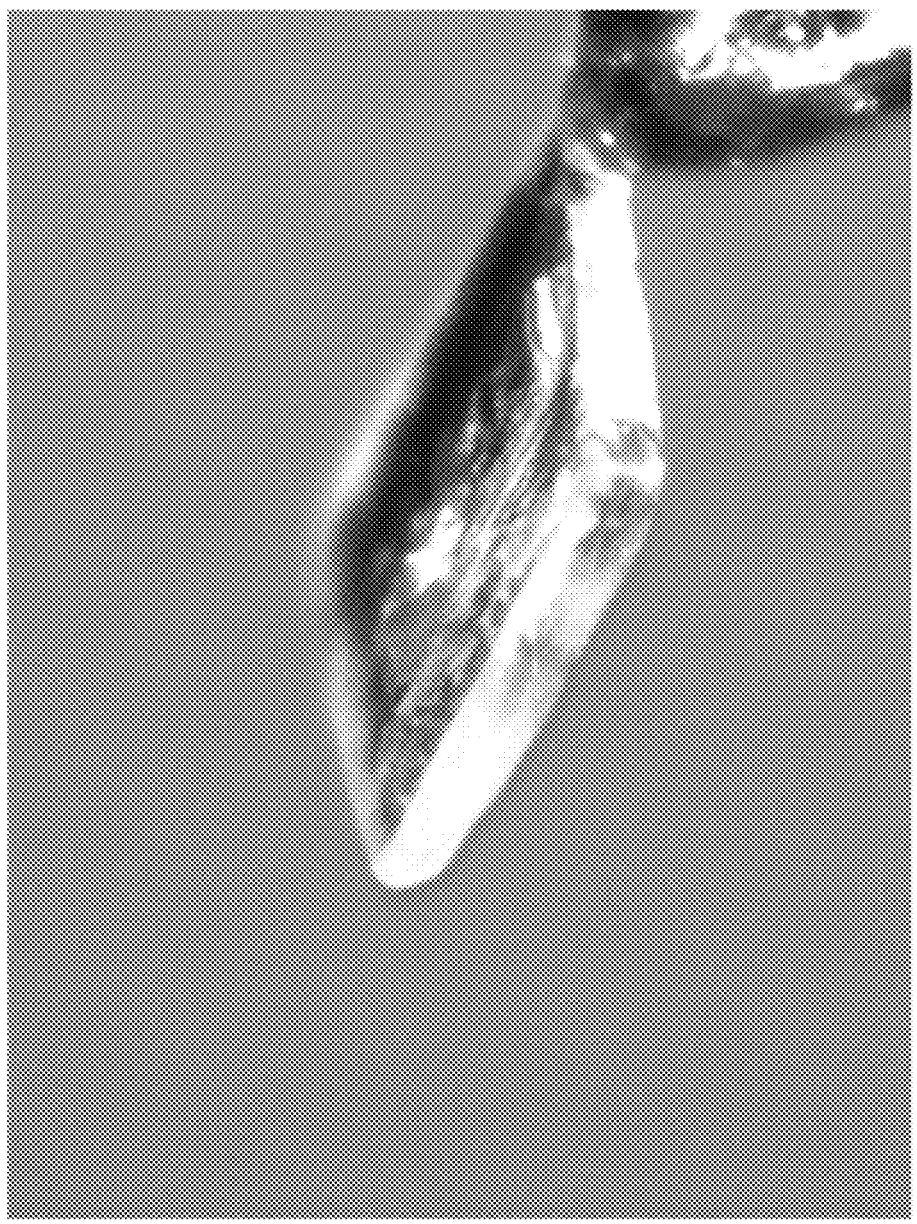
FIG. 20 is an image of a single anhydrous crystal from recrystallized CV-8972 mounted on a tip of a glass fiber.

FIG. 20 is an image of a single anhydrous crystal from recrystallized CV-8972 mounted on a tip of a glass fiber. The colorless crystal was subsequently set up on the SCXRD instrument.

Single Crystal Structure Determination

A colorless crystal was mounted on a tip of a glass fiber. The X-ray intensity data were measured at 102K temperature on a Bruker D8 Quest PHOTON 100 CMOS X-ray diffractometer system with Incoatec Microfocus Source (IμS) monochromated Mo Kα radiation (λ=0.71073 Å, sealed tube) using omega/phi-scan technique. The data were collected in 1660 frames with 10 second exposure times. Crystallographic data: $C_{22}H_{32}O_5N_3Cl_3$: a=6.9940(6) Å, b=10.5742(9) Å, c=17.5786(14) Å, α=78.252(2)°, β=82.823(2)°, γ=82.476(2)°, V=1255.37(18) Å$^3$, Z=2, F. W.=524.85, μ=0.403 mm-1, d=1.389 g/cm$^3$, F(000)=552.

Crystal data and structure refinement for j1_a are provided in Table 12.

TABLE 12

| j1_a | |
|---|---|
| Crystal data | |
| Chemical formula | $C_{22}H_{32}Cl_3N_3O_5$ |
| Mr | 524.85 |
| Crystal system, space group | Triclinic, P-1 |
| Temperature (K) | 102 |
| a, b, c (Å) | 6.9940 (6), 10.5742 (9), 17.5786 (14) |
| α, β, γ (°) | 78.252 (2), 82.823 (2), 82.476 (2) |
| V (Å$^3$) | 1255.37 (18) |
| Z | 2 |
| Radiation type | Mo Kα |
| μ (mm$^{-1}$) | 0.40 |
| Crystal size (mm) | 0.29 × 0.23 × 0.06 |
| Data collection | |
| Diffractometer | Bruker D8 Quest PHOTON 100 CMOS |
| Absorption correction | Multi-scan BRUKER SADABS |
| $T_{min}$, $T_{max}$ | 0.687, 0.747 |
| No. of measured, independent and observed [I > 2σ(I)] reflections | 30843, 8732, 7553 |
| $R_{int}$ | 0.027 |
| (sin θ/λ)$_{max}$ (Å$^{-1}$) | 0.746 |
| Refinement | |
| R[F$^2$ > 2σ(F$^2$)], wR(F$^2$), S | 0.033, 0.098, 1.01 |
| No. of reflections | 8732 |
| No. of parameters | 310 |
| No. of restraints | 3 |
| H-atom treatment | H atoms treated by a mixture of independent and constrained refinement |
| Δ⟩$_{max}$, Δ⟩$_{min}$ (e Å$^{-3}$) | 0.55, −0.46 |

Atomic coordinates (×10$^4$) and equivalent isotropic displacement parameters (Å$^2$×10$^3$) for j1_a are provided in Table 13. U(eq) is defined as one third of the trace of the orthogonalized Uij tensor

TABLE 13

| | x | y | z | U(eq) |
|---|---|---|---|---|
| Cl(1) | 3641(1) | 9477(1) | 6048(1) | 14(1) |
| Cl(2) | 11992(1) | 5170(1) | 5985(1) | 13(1) |
| Cl(3) | 1821(1) | 10077(1) | 2138(1) | 17(1) |
| O(1) | 11846(1) | 6620(1) | 2868(1) | 16(1) |
| O(2) | 9860(1) | 7793(1) | 3643(1) | 12(1) |
| O(3) | 7371(1) | 5399(1) | 8524(1) | 14(1) |
| O(4) | 6912(1) | 6708(1) | 9782(1) | 14(1) |
| O(5) | 4066(1) | 8571(1) | 9907(1) | 16(1) |
| N(1) | 5606(1) | 8451(1) | 2202(1) | 15(1) |
| N(2) | 9414(1) | 7581(1) | 5446(1) | 9(1) |
| N(3) | 6144(1) | 6997(1) | 6601(1) | 9(1) |
| C(1) | 5518(2) | 7647(1) | 1711(1) | 18(1) |
| C(2) | 6990(2) | 6666(1) | 1628(1) | 18(1) |
| C(3) | 8550(2) | 6526(1) | 2067(1) | 15(1) |
| C(4) | 8618(2) | 7383(1) | 2564(1) | 12(1) |
| C(5) | 7105(2) | 8356(1) | 2629(1) | 14(1) |
| C(6) | 10306(2) | 7218(1) | 3030(1) | 12(1) |
| C(7) | 11386(2) | 7722(1) | 4138(1) | 13(1) |
| C(8) | 10548(2) | 8407(1) | 4797(1) | 11(1) |
| C(9) | 8935(2) | 8244(1) | 6132(1) | 11(1) |
| C(10) | 7968(2) | 7358(1) | 6820(1) | 11(1) |
| C(11) | 6595(2) | 6347(1) | 5908(1) | 11(1) |
| C(12) | 7583(1) | 7222(1) | 5220(1) | 10(1) |
| C(13) | 5051(2) | 6149(1) | 7265(1) | 12(1) |
| C(14) | 4672(2) | 6764(1) | 7977(1) | 11(1) |
| C(15) | 5894(1) | 6385(1) | 8580(1) | 11(1) |
| C(16) | 5670(1) | 7028(1) | 9206(1) | 11(1) |
| C(17) | 4153(2) | 8022(1) | 9262(1) | 12(1) |
| C(18) | 2891(2) | 8375(1) | 8683(1) | 13(1) |
| C(19) | 3177(2) | 7754(1) | 8045(1) | 12(1) |
| C(20) | 7254(2) | 4307(1) | 9160(1) | 17(1) |
| C(21) | 8819(2) | 7087(1) | 9516(1) | 18(1) |
| C(22) | 2481(2) | 9539(1) | 10007(1) | 21(1) |

Bond lengths [Å] for j1_a are provided in Table 14.

TABLE 14

| O(1) | C(6) | 1.2075(13) |
|---|---|---|
| O(2) | C(6) | 1.3282(12) |
| O(2) | C(7) | 1.4443(13) |
| O(3) | C(15) | 1.3774(12) |
| O(3) | C(20) | 1.4371(14) |
| O(4) | C(16) | 1.3774(13) |
| O(4) | C(21) | 1.4372(14) |
| O(5) | C(17) | 1.3658(13) |
| O(5) | C(22) | 1.4268(14) |
| N(1) | H(1) | 0.868(14) |
| N(1) | C(1) | 1.3404(15) |
| N(1) | C(5) | 1.3460(14) |
| N(2) | H(2) | 0.881(13) |
| N(2) | C(8) | 1.4972(13) |
| N(2) | C(9) | 1.4964(13) |
| N(2) | C(12) | 1.5025(13) |
| N(3) | H(3) | 0.868(13) |
| N(3) | C(10) | 1.4937(13) |
| N(3) | C(11) | 1.4993(13) |
| N(3) | C(13) | 1.5099(13) |
| C(1) | C(2) | 1.3793(17) |
| C(2) | C(3) | 1.3893(16) |
| C(3) | C(4) | 1.3898(15) |
| C(4) | C(5) | 1.3874(15) |
| C(4) | C(6) | 1.4909(15) |
| C(7) | C(8) | 1.5071(14) |
| C(9) | C(10) | 1.5162(14) |
| C(11) | C(12) | 1.5160(14) |
| C(13) | C(14) | 1.5052(14) |
| C(14) | C(19) | 1.3915(14) |
| C(14) | C(15) | 1.4062(14) |
| C(15) | C(16) | 1.3903(14) |
| C(16) | C(17) | 1.4014(14) |
| C(17) | C(18) | 1.3922(15) |
| C(18) | C(19) | 1.3926(15) |

Angles [deg] for j1_a are provided in Table 15.

TABLE 15

| | | | |
|---|---|---|---|
| C(6) | O(2) | C(7) | 116.27(8) |
| C(15) | O(3) | C(20) | 113.71(8) |
| C(16) | O(4) | C(21) | 112.87(8) |
| C(17) | O(5) | C(22) | 116.45(9) |
| H(1) | N(1) | C(1) | 115.0(12) |
| H(1) | N(1) | C(5) | 122.2(12) |
| C(1) | N(1) | C(5) | 122.73(10) |
| H(2) | N(2) | C(8) | 108.6(11) |
| H(2) | N(2) | C(9) | 105.1(11) |
| C(8) | N(2) | C(9) | 110.24(8) |
| H(2) | N(2) | C(12) | 109.0(11) |
| C(8) | N(2) | C(12) | 114.11(8) |
| C(9) | N(2) | C(12) | 109.30(8) |
| H(3) | N(3) | C(10) | 107.1(11) |
| H(3) | N(3) | C(11) | 107.3(11) |
| C(10) | N(3) | C(11) | 109.71(8) |
| H(3) | N(3) | C(13) | 108.8(11) |
| C(10) | N(3) | C(13) | 113.17(8) |
| C(11) | N(3) | C(13) | 110.51(8) |
| N(1) | C(1) | C(2) | 120.40(11) |
| C(1) | C(2) | C(3) | 118.57(10) |
| C(2) | C(3) | C(4) | 119.88(10) |
| C(5) | C(4) | C(3) | 119.57(10) |
| C(5) | C(4) | C(6) | 121.37(9) |
| C(3) | C(4) | C(6) | 119.05(9) |
| N(1) | C(5) | C(4) | 118.85(10) |
| O(1) | C(6) | O(2) | 125.57(10) |
| O(1) | C(6) | C(4) | 123.74(10) |
| O(2) | C(6) | C(4) | 110.67(9) |
| O(2) | C(7) | C(8) | 107.00(8) |
| N(2) | C(8) | C(7) | 113.78(8) |
| N(2) | C(9) | C(10) | 110.57(8) |
| N(3) | C(10) | C(9) | 109.72(8) |
| N(3) | C(11) | C(12) | 111.10(8) |
| N(2) | C(12) | C(11) | 109.69(8) |
| C(14) | C(13) | N(3) | 110.97(8) |
| C(19) | C(14) | C(15) | 118.22(9) |
| C(19) | C(14) | C(13) | 121.58(9) |
| C(15) | C(14) | C(13) | 120.14(9) |
| O(3) | C(15) | C(16) | 120.40(9) |
| O(3) | C(15) | C(14) | 118.90(9) |
| C(16) | C(15) | C(14) | 120.65(9) |
| O(4) | C(16) | C(15) | 121.32(9) |
| O(4) | C(16) | C(17) | 118.62(9) |
| C(15) | C(16) | C(17) | 120.07(9) |
| O(5) | C(17) | C(18) | 125.51(9) |
| O(5) | C(17) | C(16) | 114.73(9) |
| C(18) | C(17) | C(16) | 119.75(9) |
| C(17) | C(18) | C(19) | 119.51(10) |
| C(18) | C(19) | C(14) | 121.71(10) |

Of the 8732 unique reflections collected to a maximum theta angle of 32.02° (0.67 Å resolution), 7553 were observed (I>2σ(I)). The linear absorption coefficient for Mo Kα radiation is 0.403 mm$^{-1}$. The data were integrated with the manufacturer's SAINT software and corrected for absorption effects using the Multi-Scan method (SADABS).

Subsequent solution and refinement were performed using the SHELXTL-2014 solution package operating on a Pentium computer. The structure was solved by direct method using SHELXTL-2014 Software Package. Non-hydrogen atomic scattering factors were taken from the literature tabulations. Non-hydrogen atoms were located from successive difference Fourier map calculations. In the final cycles of each refinement, all the non-hydrogen atoms were refined in anisotropic displacement parameters. Except for H(1), H(2), H(3) on N(1), N(2), N(3) atoms of the molecule that were located from difference Fourier map and refined with proper restraints, the rest of hydrogen atom positions were calculated and allowed to ride on the carbon to which they are bonded, assuming a C—H bond length of m Å (m=0.990 for $CH_2$ groups, m=0.980 for $CH_3$ groups, m=0.950 for Ph-H groups). Hydrogen atom temperature factors were fixed at n (n=1.2 for $CH_2$, Ph-H groups, n=1.5 for $CH_3$) times the isotropic temperature factor of the C-atom to which they are bonded. The crystal system of compound is triclinic, space group P-1 (No. 2) and the final residual values based on 310 variable parameters and 7553 observed reflections (I>2σ(1)) are $R_1$=0.0328, wR2=0.0926, and those for all unique reflections are $R_1$=0.0408, wR2=0.0975. The goodness-of-fit indicator for all data is 1.014. Peaks on the final difference map, ranging from 0.549 to −0.459 e/Å$^3$, are of no chemical significance. The efforts have been made to resolve as many alerts as possible generated by CheckCIF program. The current highest alerts are at level G.

Figure 21:
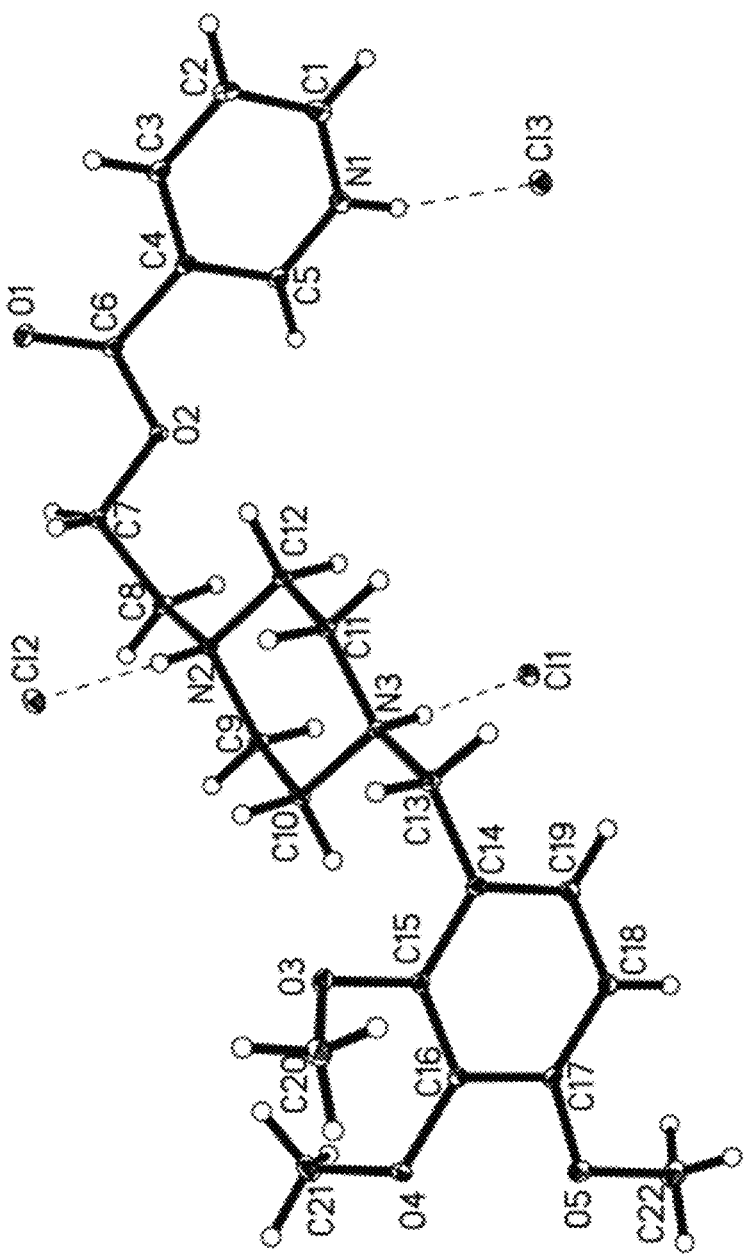
FIG. 21 is a thermal ellipsoid diagram of an asymmetric unit of the $C_{22}H_{32}Cl_3N_3O_5$ crystal.

FIG. 21 is a thermal ellipsoid diagram of an asymmetric unit of the $C_{22}H_{32}Cl_3N_3O_5$ crystal. The diagram demonstrates that this form is an anhydrate, tris-HCl salt form.

Figure 22:
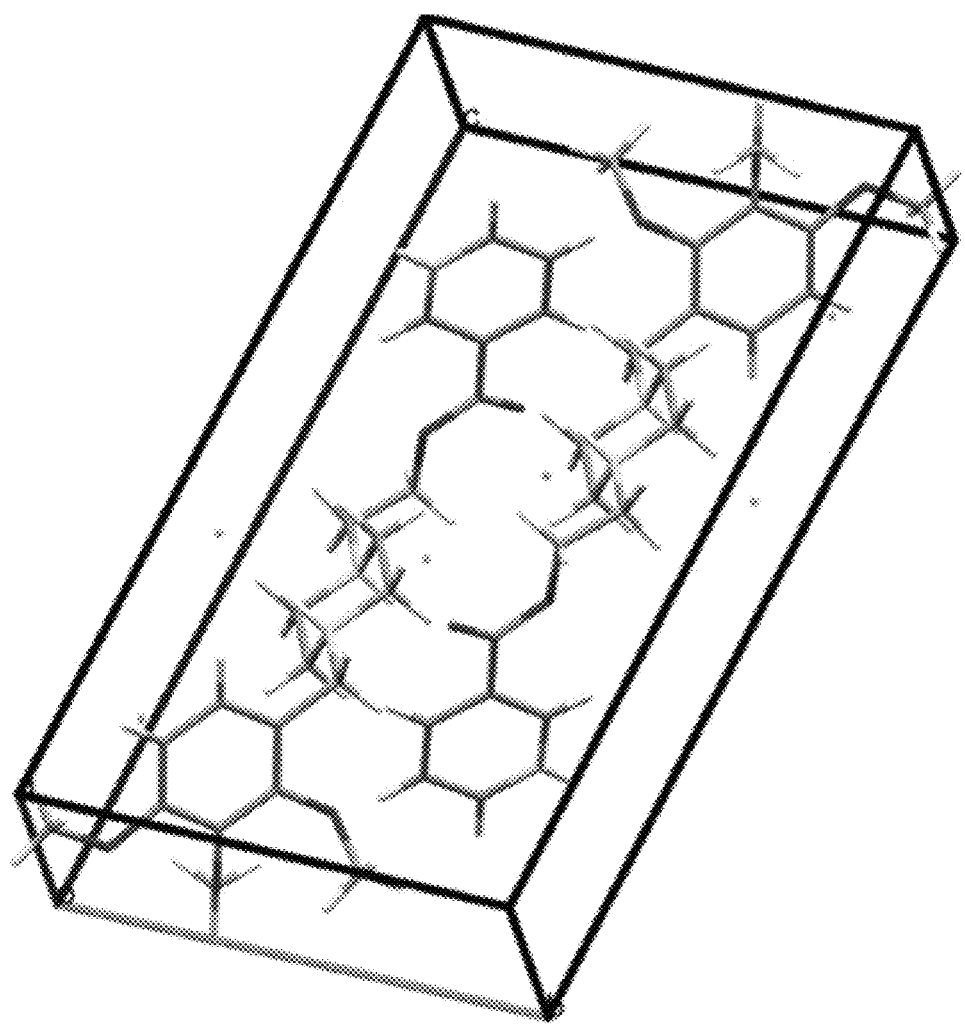
FIG. 22 shows one unit cell of the $C_{22}H_{32}Cl_3N_3O_5$ crystal.

FIG. 22 shows one unit cell of the $C_{22}H_{32}Cl_3N_3O_5$ crystal.

Figure 23:
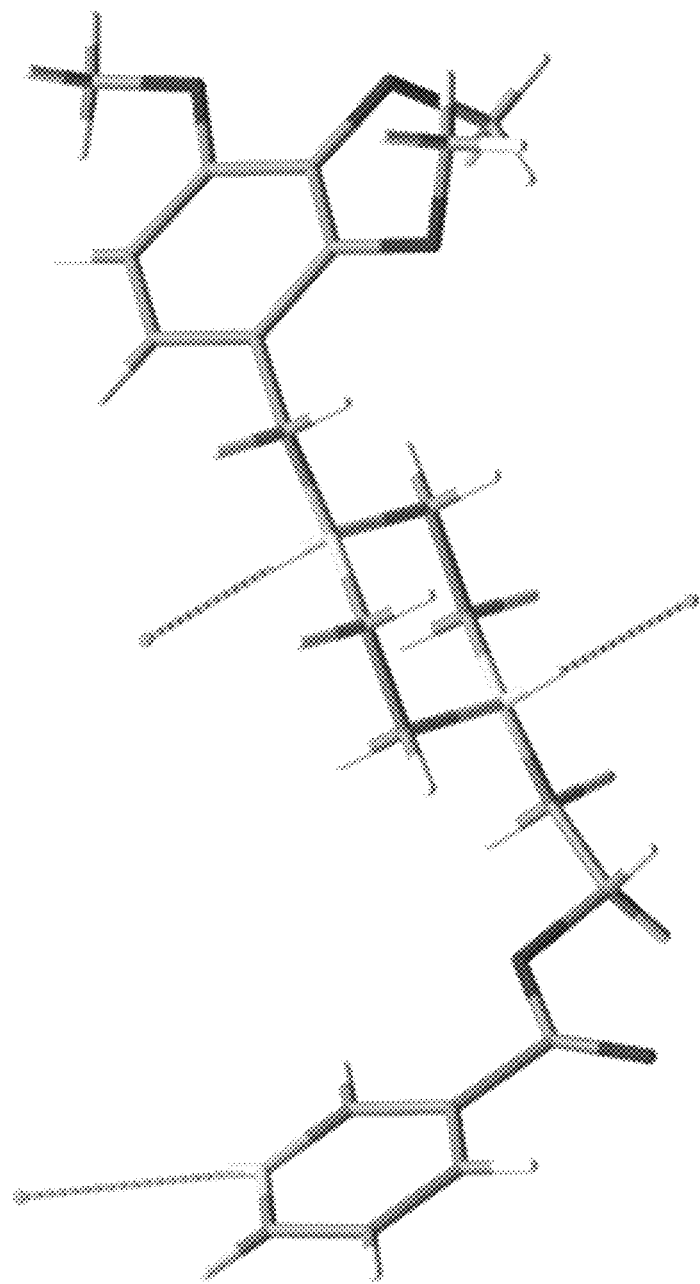
FIG. 23 is a diagram of hydrogen bonds networks and counter-ion pairs in the $C_{22}H_{32}Cl_3N_3O_5$ crystal.

FIG. 23 is a diagram of hydrogen bonds networks and counter-ion pairs in the $C_{22}H_{32}Cl_3N_3O_5$ crystal.

Figure 24:
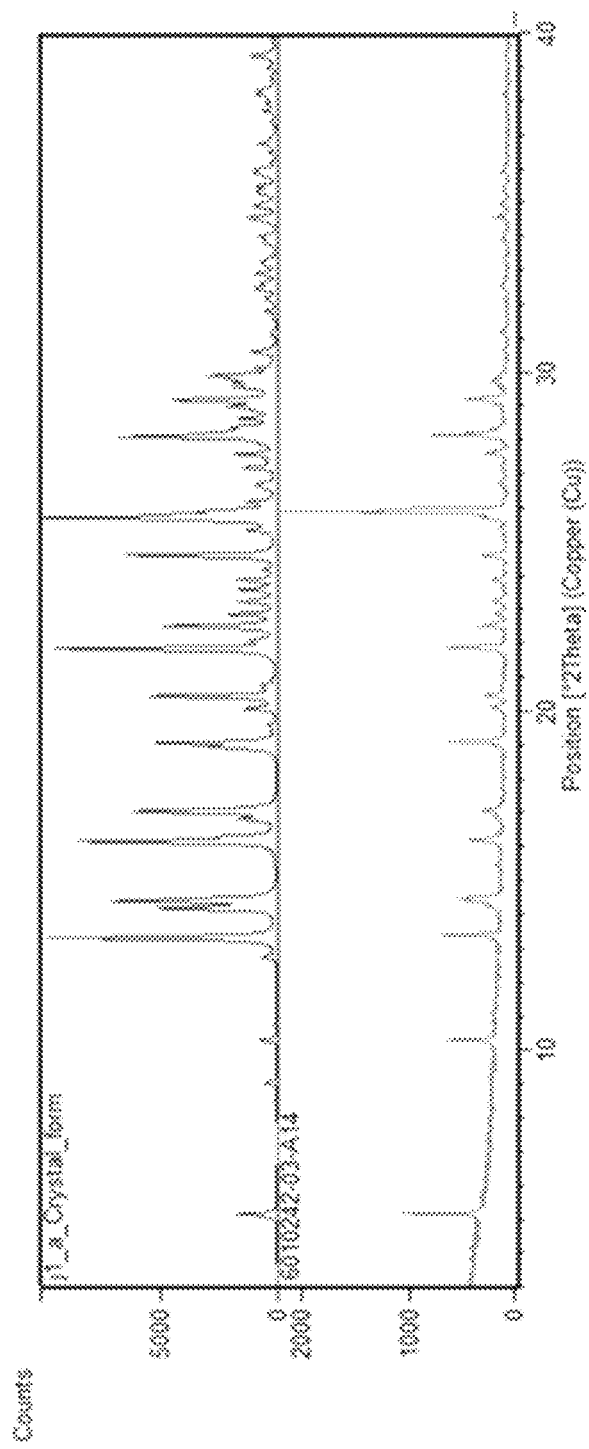
FIG. 24 shows calculated and measured XRPD diagrams of the $C_{22}H_{34}Cl_3N_3O_6$ crystal.

FIG. 24 shows calculated and measured XRPD diagrams of the $C_{22}H_{34}Cl_3N_3O_6$ crystal. Calculated XRPD diffractogram is shown in red; and measured XRPD diffractogram is shown in green.

The compound crystallizes in triclinic, space group P-1 (No. 2). The asymmetric unit contains one molecule in the form of cation/anion salt (an an hydrate tri-HCl salt) with formula of $C_{22}H_{32}O_5N_3Cl_3$. There might be some intramolecular H-bonding between N(1)-H(1) . . . Cl(3) (with distance of 2.9634(10)), N(2)-H(2) . . . Cl(2) (with distance of 2.9822(9)), N(3)-H(3) . . . Cl(1) (with distance of 3.0120(9)). Structure solution, refinement and the calculation of derived results were performed using the SHELXTL-2014 package of computer programs. Neutral atom scattering factors were those of Cromer and Waber, and the real and imaginary anomalous dispersion corrections were those of Cromer.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A crystal comprising a Form A polymorph of a monohydrate hydrochloride salt of a compound of Formula (X):

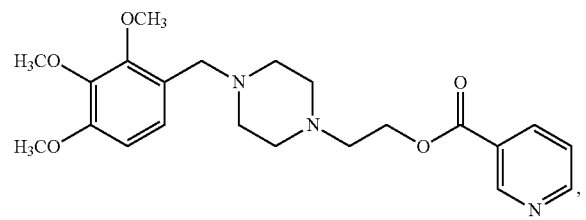

(X)

wherein the Form A polymorph has an XRPD pattern as shown in FIG. 4.

2. The crystal of claim 1, wherein the crystal is substantially free of polymorphs of Form B, Form C, Form D, and Form E.

3. A pharmaceutical composition comprising a crystal comprising a Form A polymorph of a monohydrate hydrochloride salt of a compound of Formula (X):

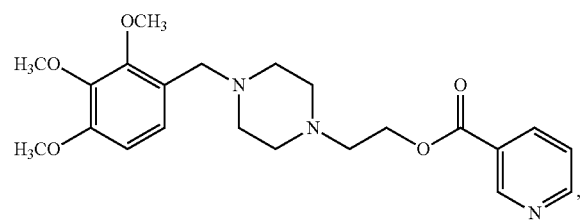

(X)

wherein the Form A polymorph has an XRPD pattern as shown in FIG. 4.

4. The composition of claim 3, wherein the composition is substantially free of polymorphs of Form B, Form C, Form D, and Form E.

5. The composition of claim 3, wherein the composition is formulated for oral administration.

6. The composition of claim 3, wherein the composition is formulated as a single unit dosage.

7. The composition of claim 3, wherein the composition is formulated as divided dosages.

8. A method of treating a condition in a subject, the method comprising providing to a subject having, or at risk of developing, a condition a composition comprising a therapeutically effective amount of a Form A polymorph of a monohydrate hydrochloride salt of a compound of Formula (X):

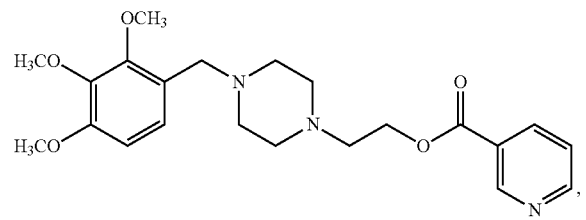

(X)

wherein the Form A polymorph has an XRPD pattern as shown in FIG. 4, and wherein the condition is selected from the group consisting of aneurysm, angina, atherosclerosis, cardiomyopathy, cerebral vascular disease, congenital heart disease, coronary artery disease, coronary heart disease, diabetic cardiomyopathy, heart attack, heart disease, heart failure, hypertension, ischemic heart disease, pericardial disease, peripheral arterial disease, rheumatic heart disease, stroke, transient ischemic attacks, and valvular heart disease.

9. The method of claim 8, wherein the composition is provided orally.

10. The method of claim 8, wherein the composition is provided as a single unit dosage.

11. The crystal of claim 1, wherein the compound has an endothermic peak at about 85.3° C. (±5° C.) and at about 214.6° C. (±5° C.) in a differential scanning calorimetry (DSC) thermogram.

12. The crystal of claim 11, wherein the compound has a DSC thermogram substantially in accordance with FIG. 5.

13. The crystal of claim 1, wherein the compound exhibits a dehydration at about 25.9° C. to about 150.0° C. with a weight loss of about 3.46% in a thermogravimetric analysis (TGA).

14. The crystal of claim 1, wherein the compound has a TGA thermogram substantially in accordance with FIG. 5.

15. The composition of claim 3, wherein the compound has an endothermic peak at about 85.3° C. (±5° C.) and at about 214.6° C. (±5° C.) in a differential scanning calorimetry (DSC) thermogram.

16. The composition of claim 15, wherein the compound has a DSC thermogram substantially in accordance with FIG. 5.

17. The composition of claim 3, wherein the compound exhibits a dehydration at about 25.9° C. to about 150.0° C. with a weight loss of about 3.46% in a thermogravimetric analysis (TGA).

18. The composition of claim 3, wherein the compound has a TGA thermogram substantially in accordance with FIG. 5.

19. The method of claim 8, wherein the compound has an endothermic peak at about 85.3° C. (±5° C.) and at about 214.6° C. (±5° C.) in a differential scanning calorimetry (DSC) thermogram.

20. The method of claim 19, wherein the compound has a DSC thermogram substantially in accordance with FIG. 5.

21. The method of claim 8, wherein the compound exhibits a dehydration at about 25.9° C. to about 150.0° C. with a weight loss of about 3.46% in a thermogravimetric analysis (TGA).

22. The method of claim 8, wherein the compound has a TGA thermogram substantially in accordance with FIG. 5.

* * * * *